US009056940B2

(12) United States Patent
Beatty et al.

(10) Patent No.: US 9,056,940 B2
(45) Date of Patent: Jun. 16, 2015

(54) ALIPHATIC POLYESTER POLYOLS FROM CYCLOHEXANE OXIDATION BYPRODUCT STREAMS AS PRECURSORS FOR POLYURETHANE AND POLYISOCYANURATE POLYMERS

(75) Inventors: Richard P. Beatty, Newark, DE (US); Carina Araullo McAdams, Wilmington, NC (US); Yanhui Sun, Wilmington, DE (US); Thomas A. Micka, West Grove, PA (US)

(73) Assignee: INVISTA North America S.a r. l., Wilmington, DE (US)

( * ) Notice: Subject to any disclaimer, the term of this patent is extended or adjusted under 35 U.S.C. 154(b) by 78 days.

(21) Appl. No.: 13/493,840

(22) Filed: Jun. 11, 2012

(65) Prior Publication Data

US 2013/0042659 A1 Feb. 21, 2013

Related U.S. Application Data

(60) Provisional application No. 61/496,268, filed on Jun. 13, 2011, provisional application No. 61/496,868, filed on Jun. 14, 2011.

(51) Int. Cl.
*C07C 35/00* (2006.01)
*C05G 3/00* (2006.01)
(Continued)

(52) U.S. Cl.
CPC ............ *C08G 18/4222* (2013.01); *C07C 31/18* (2013.01); *C05G 3/0029* (2013.01);
(Continued)

(58) Field of Classification Search
USPC ............................................. 71/31–63, 64.07
See application file for complete search history.

(56) References Cited

U.S. PATENT DOCUMENTS 3,365,490 A   1/1968   Arthur
4,233,408 A   11/1980  Satterly et al.
(Continued)

FOREIGN PATENT DOCUMENTS

PL      93248     *  5/1977
PL      151999    * 10/1990
(Continued)

OTHER PUBLICATIONS

International Search Report and Written Opinion received for PCT Patent Application No. PCT/US2012/041951, mailed on Nov. 7, 2012, 10 pages.
(Continued)

*Primary Examiner* — Wayne Langel
(74) *Attorney, Agent, or Firm* — Ni Yan

(57) ABSTRACT

The invention provides polyester polyol compositions and resin blends, useful as components of polyurethane and polyisocyanurate polymers, produced from cyclohexane oxidation reaction byproducts, such as water extracts and non-volatile distillation residues from the reaction. Such byproducts of industrial processes for preparation of adipic acid and caprolactam, important intermediates in the production of various types of nylon, have hitherto largely been used only as fuels. The present invention provides value-added products, methods for making, and methods for using the byproduct-derived polyester polyol compositions. For example, the invention provides polyurethane (PU) and/or polyisocyanurate (PIR) polymers made using the polyol compositions and polyfunctional isocyanates. The PU and PIR polymers can be used as adhesives, binders (e.g., for wood fibers), coatings (e.g., for controlled release fertilizers), and foams.

19 Claims, 1 Drawing Sheet

(51) Int. Cl.
    *C08G 18/42*    (2006.01)
    *C08G 18/10*    (2006.01)
    *C09D 175/06*   (2006.01)
    *C05C 9/00*     (2006.01)
    *C07C 31/18*    (2006.01)
    *C08G 101/00*   (2006.01)

(52) U.S. Cl.
    CPC ........... *C08G 18/10* (2013.01); *C08G 18/4286* (2013.01); *C08G 2101/00* (2013.01); *C08G 2105/02* (2013.01); *C09D 175/06* (2013.01); *C05C 9/005* (2013.01)

(56) References Cited

U.S. PATENT DOCUMENTS

| | | | |
|---|---|---|---|
| 4,804,403 A * | 2/1989 | Moore | 71/28 |
| 5,374,292 A | 12/1994 | Detrick et al. | |
| 5,435,821 A | 7/1995 | Duvdevani et al. | |
| 5,538,531 A * | 7/1996 | Hudson et al. | 71/28 |
| 5,547,486 A | 8/1996 | Detrick et al. | |
| 5,599,374 A | 2/1997 | Detrick | |
| 5,803,946 A | 9/1998 | Petcavich et al. | |
| 5,851,261 A * | 12/1998 | Markusch et al. | 71/64.07 |
| 6,338,746 B1 | 1/2002 | Detrick et al. | |
| 6,537,611 B1 | 3/2003 | Detrick et al. | |
| 6,663,686 B1 | 12/2003 | Geiger et al. | |
| 6,682,751 B1 | 1/2004 | Hargrove et al. | |
| 7,267,707 B2 | 9/2007 | Rosenthal et al. | |
| 7,544,736 B2 | 6/2009 | Zhou et al. | |
| 7,682,656 B2 | 3/2010 | Xing et al. | |
| 7,713,326 B2 | 5/2010 | Carstens et al. | |
| 7,771,505 B2 | 8/2010 | Ogle et al. | |
| 8,759,594 B2 | 6/2014 | Abillard et al. | |
| 2004/0016276 A1 | 1/2004 | Wynnyk et al. | |
| 2004/0020254 A1 | 2/2004 | Wynnyk et al. | |
| 2004/0045331 A1 | 3/2004 | Geiger et al. | |
| 2004/0054235 A1 | 3/2004 | Fodor et al. | |
| 2004/0105877 A1 | 6/2004 | Hargrove et al. | |
| 2005/0276905 A1 | 12/2005 | Xing et al. | |
| 2006/0000252 A1 | 1/2006 | Carstens et al. | |
| 2006/0115586 A1 | 6/2006 | Xing et al. | |
| 2006/0222735 A1 | 10/2006 | Rosenthal et al. | |
| 2007/0137274 A1 | 6/2007 | Wynnyk et al. | |
| 2007/0231369 A1 | 10/2007 | Hargrove | |
| 2008/0010878 A1 | 1/2008 | Hansen et al. | |
| 2008/0236228 A1 | 10/2008 | Geiger et al. | |
| 2010/0011825 A1 | 1/2010 | Ogle et al. | |
| 2010/0186470 A1 | 7/2010 | Xing et al. | |
| 2010/0233325 A1 | 9/2010 | Hargrove | |
| 2010/0233332 A1 | 9/2010 | Xing et al. | |
| 2010/0275665 A1 | 11/2010 | Ogle et al. | |
| 2010/0307211 A1 | 12/2010 | Xing et al. | |
| 2010/0326152 A1 * | 12/2010 | Mente | 71/27 |
| 2012/0064252 A1 | 3/2012 | Beatty | |
| 2012/0101009 A1 | 4/2012 | Beatty | |
| 2012/0227451 A1 * | 9/2012 | Ogle et al. | 71/28 |
| 2012/0240648 A1 * | 9/2012 | Ogle et al. | 71/28 |

FOREIGN PATENT DOCUMENTS

| | | |
|---|---|---|
| PL | 162632 * | 12/1993 |
| WO | 2009/022432 A1 | 2/2009 |
| WO | 2010/088227 A1 | 8/2010 |
| WO | 2010/115759 A2 | 10/2010 |
| WO | 2012/173938 A1 | 12/2012 |

OTHER PUBLICATIONS

International Preliminary Report on Patentability received for PCT Patent Application No. PCT/US2012/041951, mailed on Jan. 3, 2014, 8 pages.

* cited by examiner

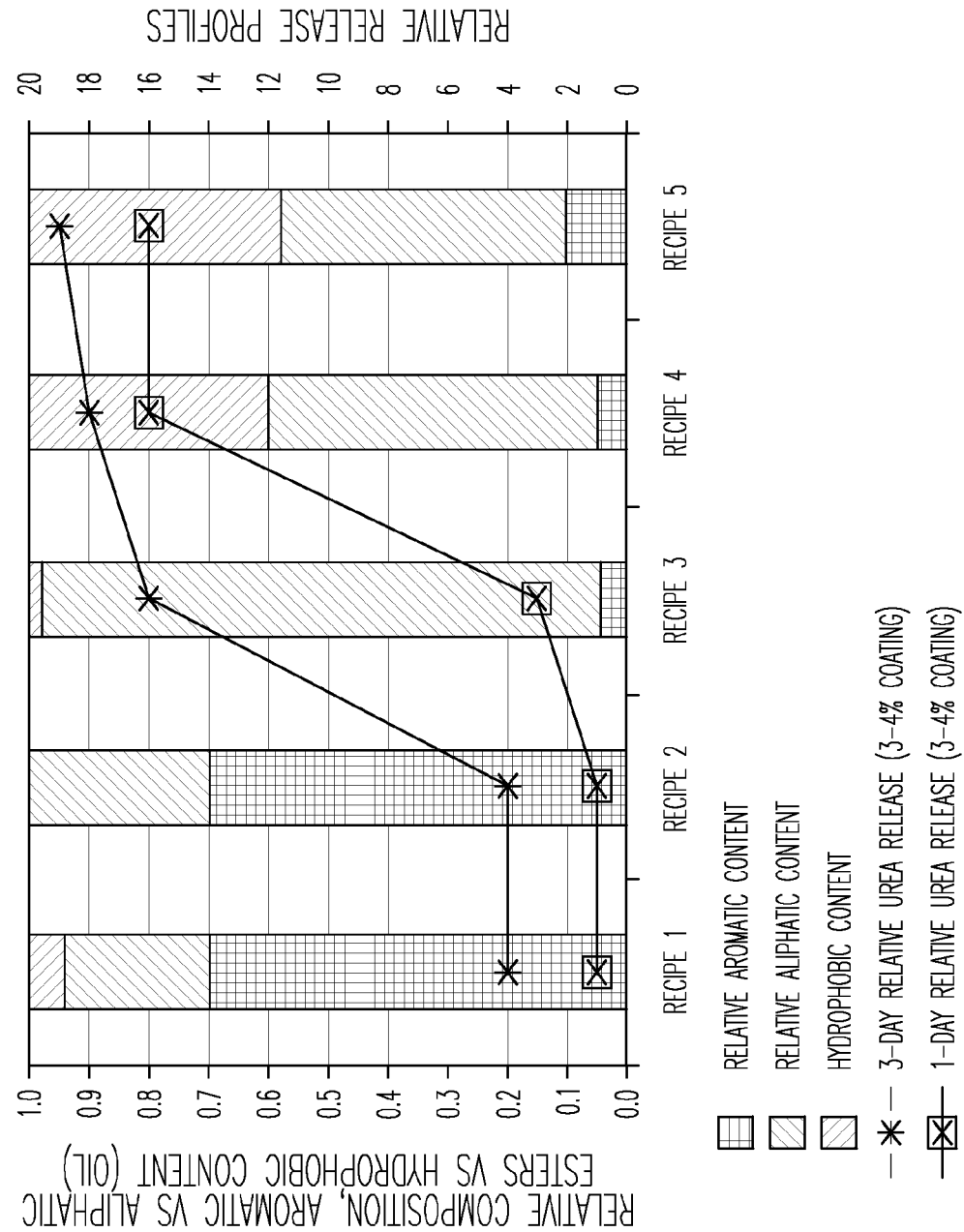

ALIPHATIC POLYESTER POLYOLS FROM CYCLOHEXANE OXIDATION BYPRODUCT STREAMS AS PRECURSORS FOR POLYURETHANE AND POLYISOCYANURATE POLYMERS

CROSS-REFERENCE TO RELATED APPLICATIONS

This application claims the benefit of priority of U.S. provisional applications 61/496,268, filed Jun. 13, 2011, and 61/496,868, filed Jun. 14, 2011, the disclosures of which are incorporated herein by reference in their entireties.

BACKGROUND

As petroleum-based materials escalate in price and environmental pressures increase, there is a growing need to responsibly utilize, to the greatest extent possible, all products from petrochemical processes, which includes the byproducts that are unavoidably formed along with the desired main products. Reaction byproducts are often mixtures that may be complex in composition, difficult to use directly, and difficult and/or costly to purify. They are frequently treated as materials of little or no value, for example being discarded or burned for fuel value.

It is known in the manufacture of adipic acid or caprolactam from cyclohexane that byproduct streams result because the chemical transformations do not proceed perfectly in 100% yield. These byproduct streams contain a variety of molecules having functionalities which include, among others, one or more alcohol, alkene, carboxylic acid, lactone, ester, and ketone groups, and combinations thereof. These byproduct streams are complex mixtures. It is known to use some byproduct streams for their fuel value. In such uses, there is little or no recognition or recovery of value for the functionality present in the byproduct stream. As a result, most of the byproduct stream from adipic acid manufacture remains underutilized.

Manufacture of adipic acid from cyclohexane generally involves two steps. First, cyclohexane is oxidized using air to a mixture of cyclohexanol (A) and cyclohexanone (K), the mixture being referred to as KA. Second, KA is oxidized using nitric acid to adipic acid.

A similar "cyclohexane oxidation" step is also performed in manufacture of caprolactam from cyclohexane. In the caprolactam manufacturing process, cyclohexanone is converted to its oxime, which is then caused to undergo molecular rearrangement to yield caprolactam. Caprolactam can then be polymerized to provide nylon-6.

In the known cyclohexane oxidation processes, cyclohexane is generally oxidized with oxygen or a gas containing oxygen, at low conversion, to produce an intermediate stream containing cyclohexanol (A), cyclohexanone (K), and cyclohexyl hydroperoxide (CHHP) in cyclohexane. CHHP is an important intermediate in oxidation of cyclohexane to KA and various processes are known in the art to optimize conversion of CHHP to KA, in order to maximize yield of KA. In addition to K, A, and CHHP, cyclohexane oxidation produces byproducts. In some cases, it has been found that these byproducts interfere with subsequent processing to convert CHHP to KA.

It is known that at least some of the interfering byproducts can be removed by contacting the intermediate stream containing K, A, and CHHP with water or caustic, for example as described in U.S. Pat. No. 3,365,490, which is incorporated herein by reference in its entirety. This patent describes air oxidation of cyclohexane, followed by nitric acid conversion to diacids, such as adipic acid, and processing of byproduct wastestreams. This contacting, or extraction results in a two-phase mixture that, after phase separation, yields a purified cyclohexane stream containing K, A, and CHHP (which can be subjected to known high-yield processes to convert CHHP to KA) and a byproduct water stream. The byproduct water stream ("Water Wash") contains various mono- and di-acids, hydroxy-acids, and other oxidation byproducts formed during the initial oxidation of cyclohexane.

Regardless of whether a water wash is performed as an intermediate step, the stream containing K, A, and CHHP is further processed by methods well known in the art, to complete conversion of CHHP to K and A. The resulting mixture is then refined, again by methods well known in the art, to recover unconverted cyclohexane for recycle and to obtain purified K and A for subsequent oxidation to adipic acid or conversion to caprolactam. To summarize, the byproduct streams, sometimes referred to herein as "by-product" streams, available from a cyclohexane oxidation process include "Water Wash" (the aqueous stream produced by water extraction of cyclohexane oxidate) and "NVR" (the high-boiling distillation bottoms from KA refining), CAS Registry Number 68411-76-7. Concentration of "Water Wash" by removal of at least some of the water produces a stream known as "COP Acid," CAS Registry Number 68915-38-8. See also published US patent applications US2004/0054235 describing production of "non-volatile residue", high-boiling distillation bottoms from distillative recovery of cyclohexane oxidation products cyclohexanol and cyclohexanone, termed "NVR", having low chromium content, more suitable for combustion, US2012/0064252 and US2012/0101009, incorporated herein by reference, describing processing of NVR, Water Wash, or COP acid through conversion of free acid functional groups to monomeric esters and oligomeric esters, and converting oligomeric esters to monomeric esters.

"Water Wash", "COP Acid", and "NVR" are known to contain both mono- and poly-functional materials (functional monomers), mainly with the functional groups comprising acids, peroxides, ketones, alcohols, and esters. Other functional groups such as aldehyde, lactone, and alkene are also known to be present. Multiple functional groups may be combined in a single molecule, such as in a hydroxyacid, for example hydroxycaproic acid or hydroxyvaleric acid. In general, the acid functional group is at one end of a linear hydrocarbyl chain, and the hydroxy group may be present in various positions along the chain. The mono- and poly-functional materials contained within these byproduct streams are primarily aliphatic. Known examples of hydroxyacids include 6-hydroxycaproic acid, 5-hydroxyvaleric acid, 3-hydroxyvaleric acid, and 3-hydroxypropionic acid. Similarly, known examples of simple mono-acids include formic acid, acetic acid, propionic acid, butyric acid, valeric acid, and caproic acid. Known examples of diacids include succinic acid, glutaric acid, and adipic acid. Known examples of keto-acids include 4-oxo valeric acid (also known as levulinic acid) and 5-oxo caproic acid. Known examples of alcohols include cyclohexanol, 1-propanol, 1-butanol, 1-pentanol, and various diols such as 1,2- 1,3-, and 1,4-cyclohexanediols, various butanediol isomers, and various pentanediol isomers.

SUMMARY

The inventors herein have discovered a new simple and economical process that provides polyols of new and unique composition from cyclohexane oxidation byproducts. It has further been found that these polyols can be used to prepare new and unique polyurethanes, and that the polyurethanes thereby obtained are useful in a wide variety of applications. By using a process of the invention, it is not necessary to first separate individual monomers such as adipic acid from the cyclohexane oxidation byproducts. Surprisingly, the complex mixtures can be used directly in a simple process that affords useful polyols. This discovery is of great value because it can eliminate the need for costly and complicated purification or separation processes. The current disclosure is focused on utilization of byproduct streams from the oxidation of cyclohexane to KA. Notably, the polyol compositions of the invention can be used as components of resin blends that can be combined with coreactants, catalysts, and other ingredients to provide pre-polymer compositions, which then can undergo polymerization to provide polymer materials useful as coatings, sealants, binders, and the like, such as coatings for controlled release fertilizer compositions.

The present invention can provide aliphatic polyester polyol compositions, methods of making polyol compositions from cyclohexane oxidation byproducts, methods of using aliphatic polyester polyol compositions such as in the formation of resin blends, pre-polymer compositions comprising the resin blends incorporating the polyol compositions, methods of making and using pre-polymer compositions incorporating the inventive polyol compositions, polyurethane (PU) and polyisocyanurate (PIR) compositions incorporating the polyol-containing pre-polymer compositions for flexible applications, polyurethane compositions for semi-rigids applications, polyurethane compositions for rigid applications, foam compositions, methods of making foam compositions, methods of using foam compositions, PU and/or PIR spray foams, methods of making PU and/or PIR foams, methods of using PU and/or PIR foams, PU coating compositions, methods of making PU coating compositions, methods of using PU coating compositions, PU adhesive compositions, methods of making PU adhesive compositions, methods of using PU adhesive compositions, PU binder compositions, methods of making PU binder compositions, methods of using PU binder compositions, and the like.

For example, the invention can provide new materials, incorporating inventive polyurethane and polyisocyanurate compositions, useful for coatings, adhesives, elastomers, sealants, binders, and the like. More specifically, the invention can provide coatings for controlled release fertilizer compositions incorporating polyol compositions prepared by methods of the invention.

The present invention can provide polyol compositions through application of processes of the invention, starting with a byproduct stream derived from cyclohexane oxidation products, wherein the polyol composition is obtained by, starting with one or more of the following: a water extract (Water Wash), a concentrated water extract (COP Acid), or a non-volatile residue (NVR); optionally heating removing at least a portion of the water and at least a portion of the free and bound monofunctional components, adding a polyhydroxy compound, and removing at least a portion of the water and at least a portion of the free and bound monofunctional components by heating, optionally under vacuum or optionally with inert gas sparge, to form a polyol composition Thus, the invention can provide polyol compositions from several sources through processing of byproduct streams of cyclohexane oxidation processes.

For example, the invention can provide a method of preparing a polyol composition, the method comprising:

heating a byproduct mixture comprising: i) a water extract of a cyclohexane oxidation reaction product, optionally concentrated; or, ii) a non-volatile residue of a cyclohexane oxidation reaction product, optionally concentrated, or a mixture thereof; and, one or more polyhydroxy compound; and optionally, a catalyst; optionally under vacuum, or optionally with an inert gas sparge; to remove monofunctional components and water by distillation.

Monofunctional components include, inter alia, monocarboxylic acids such as formic acid, acetic acid, and the like; and also monofunctional components include monohydroxy compounds, i.e., monohydric alcohols, such as cyclohexanol.

Further, the method can include a step of heating the byproduct mixture, optionally under vacuum, or optionally with an inert gas sparge, to remove monofunctional components and water, prior to adding the one or more polyhydroxy compounds, then continuing to heat the resulting mixture. A polyol can be a glycol, or can be a triol, tetraol, or higher polyol such as a saccharide, sugar alcohol, and the like.

The method can further include adding polycarboxylic acids, or esters or anhydrides thereof; or adding hydrophobic materials; or any combination thereof; before or during the heating and distillation process.

The heating and distillation process can use vacuum, inert gas sparge, superheated steam, special equipment such as various types of evaporators, or combinations thereof, to enhance mass transfer and removal of water and monofunctional components.

The relative amount of polyhydroxy compounds and other optional components that are added can be adjusted to provide a polyol product with a favorably low acid number (as determined by standard ASTM method, incorporated by reference herein, preferably less than 10 mg KOH/gm of sample, more preferably less than 5 mg KOH/gm of sample) and a favorably high OH number (a standard value in polyol chemistry, determined by an ASTM method incorporated by reference herein) of about 30 to about 500 mg KOH/gm of sample or of about 100 to about 500 mg KOH/gm of sample. If appropriate acid and OH numbers are not initially achieved, the product obtained can be reheated in the presence of additional polyol (glycol).

For example, a remaining content of the monofunctional components following the step of heating can be about 10% or less, or can be about 5% or less, or can be 2% or less of the reaction mixture, by weight. For example, the method can comprise adding the catalyst to the byproduct mixture, then heating to remove monofunctional components; and/or, the method can comprise adding a polyhydroxy compound then heating to remove monofunctional components, or can comprise heating prior to, concurrent with, and/or subsequent to addition of the polyhydroxy compound. A polyhydroxy compound can be a: diol (glycol), triol, or higher functionality polyols, including but not limited to ethylene glycol, diethylene glycol, polyethylene glycol, propylene glycol, dipropylene glycol, polypropylene glycol, butanediol, pentanediol, hexanediol, glycerine, trimethylolpropane, pentaerythritol, sorbitol, or a combination thereof.

Additionally, a third composition comprising a polyfunctional (i.e., polycarboxylic) acid, ester, or anhydride; and/or a hydrophobic material; can be added, e.g., prior to or concurrently with heating the mixture to remove water and monofunctional components. Examples include polyfunctional aromatic acids, anhydrides, and polyfunctional esters thereof, (e.g., a diol monoester), and polyfunctional aliphatic acids, anhydrides, and polyfunctional esters thereof.

A polycarboxylic acid can be a: diacid, triacid, or higher-functionality polycarboxylic acid or corresponding ester or anhydride including but not limited to polyfunctional aromatic acids, polyfunctional aromatic anhydrides, and polyfunctional aromatic esters (e.g., a diol monoester), and polyfunctional aliphatic acids, anhydrides, and polyfunctional esters thereof such as succinic acid, glutaric acid, adipic acid, phthalic acid, terephthalic acid, sebacic acid, azelaic acid, dodecanedioic acid, citric acid, succinic anhydride, phthalic anhydride, dimethyl succinate, dimethyl glutarate, dimethyl adipate, dimethyl terephthalate and a combination thereof.

A hydrophobic material can be a plant oil (i.e., a plant-derived oil), or a fatty acid or ester derived therefrom; an animal oil (i.e., an animal-derived oil), or a fatty acid or ester derived therefrom; or a synthetic oil, synthetic fatty acid, or synthetic fatty ester. By an oil is meant a hydrophobic compound regardless of its physical state at room temperature; i.e., an oil can be a solid, such as a solid fat, at room temperature.

Thus, more specifically, the invention can provide a method of making an aliphatic polyester polyol, comprising processing a byproduct mixture from a water extract (Water Wash), or a concentrated water extract (COP Acid), or a non-volatile residue (NVR), or mixture thereof, by adding one or more polyhyhydroxy compound, and removing by heating and distillation at least a portion of the water along with free and bound monofunctional components from the mixture, so that about 10% or less, or 5% or less, or 2% or less by weight, of total monofunctional components remain in the mixture. Optionally, a third composition, or a hydrophobic material, or both, can be added to the byproduct mixture, with heating and distillation; thus forming the aliphatic polyester polyol.

Accordingly, a method of the invention can further comprise adding a polycarboxylic acid, ester, or anhydride then heating to remove monofunctional components; and/or the method can comprise adding a hydrophobic material then heating to remove monofunctional components. Then, if the acid number and OH number are not optimal for a planned use, they can be further adjusted by adding additional polyhydroxy compound (e.g., glycol), and further heating, optionally in the presence of a catalyst, with distillation to remove any further monofunctional components and/or water.

The invention can provide a composition prepared by a method as described above. Compositions prepared by methods of the invention can further include one or more other components known to those skilled in the art and dependent on end use. Such components may include other polyols, solvents, catalysts, chain extenders, crosslinking agents, curatives, surfactants, blowing agents, fillers, flame retardants, plasticizers, light stabilizers, colorants, waxes, biocides, minerals, micronutrients, inhibitors, stabilizers or other organic or inorganic additives.

A polyol composition of the invention or prepared by a method of the invention, can be used in formation of a resin blend, suitable as an "B-side" component of a pre-polymer composition. The resin blend comprises the polyol composition and can further comprise the other polyols, solvents, catalysts, chain extenders, crosslinking agents, curatives, surfactants, blowing agents, fillers, flame retardants, plasticizers, light stabilizers, colorants, waxes, biocides, minerals, micronutrients, inhibitors, stabilizers or other organic or inorganic additives.

The resin blend of the invention can be reacted with a polyfunctional isocyanate ("A-side component"), such as methylene diphenyl diisocyanate (MDI) or a polymeric MDI (PMDI), to provide a pre-polymer composition of the invention, that upon reaction of the A-side and B-side components can provide an inventive polyurethane or a polyisocyanurate, depending upon the specific conditions used. Thus, the invention further provides polyurethane or polyisocyanurate polymer compositions, methods of preparing the polymer compositions, and methods of using the polymer compositions.

Thus, more specifically, the invention can provide a method of making an aliphatic polyester polyol, comprising processing a byproduct mixture from a water extract (Water Wash), or a concentrated water extract (COP Acid), or a non-volatile residue (NVR), or mixture thereof, by adding one or more polyhyhydroxy compound, and removing by heating and distillation at least a portion of the water along with free and bound monofunctional components from the mixture, so that about 10% or less, or 5% or less, or 2% or less by weight, of total monofunctional components remain in the mixture. Optionally, a third composition, or a hydrophobic material, or both, can be added to the byproduct mixture, with heating and distillation; thus forming the aliphatic polyester polyol.

Accordingly, a method of the invention can further comprise adding a polycarboxylic acid, ester, or anhydride then heating to remove monofunctional components; and/or the method can comprise adding a hydrophobic material then heating to remove monofunctional components. Then, if the acid number and OH number are not optimal for a planned use, they can be further adjusted by adding additional polyhydroxy compound (e.g., glycol), and further heating, optionally in the presence of a catalyst, with distillation to remove any further monofunctional components and/or water, until the acid number is sufficiently low and the OH value is sufficiently high.

The invention can provide a polyurethane (PU) or polyisocyanurate (PIR) polymer from a polyol of the invention or prepared by a method of the invention, by reacting the polyol composition with a polyfunctional isocyanate to provide a PU or PIR pre-polymer composition, which upon standing under suitable conditions can set up to provide a PU or PIR polymer. It is known to use various amines and polyamines as curatives, crosslinkers, or chain extenders and it should be understood that when primary or secondary amines are used as such that urea linkages may be present in the resulting polymer. A polymer of the invention can be useful as a coating, e.g., a controlled release fertilizer coating; an adhesive; a sealant; or a binder, e.g., a wood binder. A PU or PR polymer of the invention or prepared by a method of the invention can be used for a fiber-reinforced composition, such as a wood fiber reinforced composite. A PU or PR polymer of the invention can further include other polyols, solvents, catalysts, chain extenders, crosslinking agents, curatives, surfactants, blowing agents, fillers, flame retardants, plasticizers, light stabilizers, colorants, waxes, biocides, minerals, micronutrients, inhibitors, stabilizers, or other organic or inorganic additives. For example, a controlled release fertilizer of the invention can include a coating containing biocides, micronutrients, and the like.

For example, a PU or PIR polymer of the invention can be used as a controlled-release fertilizer coating, as taught in published U.S. Patent Applications 2010/0307211 to Xing et al., 2010/0275665 to Ogle et al., 2010/0233332 to Xing et al., 2010/0186470 to Xing et al., U.S. Pat. No. 7,544,736B2 to Kazemizadeh et al., published U.S. Application 2008/010878A1 to Kazemizadeh, U.S. Pat. No. 7,267,707 to Rosenthal et al., published U.S. Patent Application 2006/0222735A1 to Rosenthal et al., U.S. Pat. No. 5,435,821 to Duvdevani et al., U.S. Pat. No. 5,538,531 to Hudson et al., all of which are incorporated by reference in their entireties. A PU or PIR coated particulate fertilizer of the invention, can be prepared by coating a particulate fertilizer material with a pre-polymer composition of the invention, then allowing the pre-polymer composition to set up to provide a polymer coating of the fertilizer material. A fertilizer coated with a polymer of the invention can provide improved, i.e., more prolonged, or better timed- or controlled-release fertilizer compositions. The inventors herein have unexpectedly discovered that by use of a third component comprising an aromatic component such as an aromatic polyacid, activated ester, polyfunctional ester, or anhydride, coated fertilizer compositions having improved extended release properties under field conditions can be obtained.

The invention can provide a foam composition, comprising a pre-polymer composition of the invention or prepared by a method of the invention, with a blowing agent. The foam composition can be a spray foam. For example, the invention can provide a spray foam extrudate fertilizer.

Accordingly, the invention provides technical solutions to the problems of enhancing the value and use of byproduct streams resulting from large scale chemical industrial operations, such as nylon manufacturing operations involving a step of cyclohexane oxidation to cyclohexanol/cyclohexanone products, by devising technically and economically feasible uses for the byproduct streams. Methods and compositions of the invention provide a higher value use for these byproduct streams than merely combusting the streams for their heat value. By using the organic components of these byproduct streams as sources of polyols useful for the synthesis of polymers such as polyurethanes and polyisocyanurates, the present invention solves the technical problems of enhancing uses and economic benefits from chemical processing operations.

BRIEF DESCRIPTION OF THE FIGURE

FIG. 1 shows a graph of fertilizer release rates under field conditions from five examples of controlled release fertilizer compositions having varying proportions of aromatic constituents with respect to aliphatic components and hydrophobic components, as related to delay of fertilizer release.

DETAILED DESCRIPTION

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the suitable methods and materials are now described.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, polymer chemistry, foam chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmospheres. Standard temperature and pressure are defined as 20° C. and 1 atmosphere absolute.

As used in this specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

All percent compositions are given as weight-percentages, unless otherwise stated. When solutions of components are referred to, percentages refer to weight-percentages of the composition including the solvent (e.g., water) unless otherwise indicated.

All average molecular weights of polymers are weight-average molecular weights, unless otherwise specified.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range includes "about 'x' to about 'y'". To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

The term "hydroxyl value" indicates the total amount of residual hydroxyl groups present in the material. The hydroxyl value, also referred to herein as hydroxyl number, is reported as mg KOH/gm (i.e., mg KOH per gram of sample), and is measured according to well-known methods such as standard ASTM D 1957 or ASTM E1899.

The term "average functionality", or "average hydroxyl functionality" of a polyol indicates the number of OH groups per molecule, on average. The average functionality of an isocyanate refers to the number of —NCO groups per molecule, on average.

The term "acid number" correspondingly indicates the concentration of carboxylic acid groups present in the material, and is reported in terms of mg KOH/g (i.e., mg KOH per gram of sample), and measured according to well-known methods such as standard ASTM D 4662 or ASTM D1613.

The amount of isocyanate (—NCO) present in the pre-polymer composition may be expressed in terms of an "isocyanate reaction index", also called "isocyanate index", "NCO index" or simply "index." Herein and conventionally in the art, an isocyanate reaction index of 100 corresponds to 1.0 isocyanate group (—NCO) per active hydrogen atom. Additional details regarding the NCO index are described in U.S. Pat. No. 6,884,824, which is incorporated herein by reference. Typical Isocyanate Indexes for sprayed polyurethane (PU) foam range from about 110 to 120. As stated in "The Polyurethanes Book" by Huntsman [The Polyurethanes Book, Ed. David Randall and Steve Lee, Wiley (2003), ISBN 0-470-85041-8], Isocyanate Index is the measure of the excess isocyanate used relative to the theoretical equivalent amount required. For example, an index of 105 indicates a 5% excess of isocyanate is being used.

The term "aliphatic group" refers to a saturated or unsaturated linear or branched hydrocarbon group and encompasses alkyl, alkenyl, and alkynyl groups, for example.

The terms "polyol" or "aliphatic polyol" refer to a polyol prepared from a mixture of aliphatic functional monomers (byproducts) from a cyclohexane oxidation process, with average functionality greater than 1. Such polyols can be prepared from water extracts or non-volatile residues that are byproduct streams resulting from cyclohexane oxidation processes.

The terms "alk" or "alkyl" refer to straight or branched chain hydrocarbon groups, which can have from 1 to 20 carbon atoms, such as from 1 to 12 carbon atoms, for example 1 to 8 carbon atoms; including groups such as methyl, ethyl, n-propyl, i-propyl, n-butyl, i-butyl, t-butyl, pentyl, hexyl, heptyl, n-octyl, dodecyl, amyl, 2-ethylhexyl, and the like. An alkyl group is optionally substituted, unless stated otherwise, with one or more groups, selected from aryl (optionally substituted), heterocyclo (optionally substituted), carbocyclo (optionally substituted), halo, hydroxy, protected hydroxy, alkoxy (e.g., $C_1$ to $C_7$) (optionally substituted), poly(oxyalkylene) (e.g., ethoxylated or propoxylated groups), acyl (e.g., $C_1$ to $C_7$), aryloxy (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like.

The terms "aromatic", "ar", or "aryl" refer to aromatic homocyclic (i.e., hydrocarbon) mono-, bi-, or tricyclic ring-containing groups, for example having 6 to 12 members such as phenyl, naphthyl, and biphenyl. An aryl group is optionally substituted, unless stated otherwise, with one or more groups, selected from alkyl (optionally substituted alkyl), alkenyl (optionally substituted), aryl (optionally substituted), heterocyclo (optionally substituted), halo, hydroxy, alkoxy (optionally substituted), poly(oxyalkylene) (e.g., ethoxylated or propoxylated groups), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and the like. Optionally, adjacent substituents, together with the atoms to which they are bonded, form a 3- to 7-member ring.

The term or phrases "monofunctional components" or "monofunctional compounds" refers to compounds in free form, or bound to other compounds by ester bonds, where each monofunctional component or compound contains only a single reactive functional group. For example, methanol is a free monofunctional component, and a methyl ester of a diacid is a bound monofunctional component. The terms are to be understood in the context in which they are used. For example, in the context of preparing a polyester polyol, reactive groups would include carboxylic acid and hydroxyl groups since those are capable of reacting with the complementary functional group in another monomeric compound to form an ester linkage. Non-reactive functional groups such as ketone or alkene are not included in determination of whether a component is monofunctional, since such groups do not participate in forming a polyester polyol. In other words, a monomeric compound containing one hydroxyl group and one ketone group would be considered a monofunctional compound in the context herein. Similarly, a monomeric compound containing one hydroxyl group would be considered a monofunctional compound in the context herein.

Monofunctional components or compounds (e.g., monoacids, mono-alcohols, and the like) can include bound and/or unbound and include: formic acid, acetic acid, cyclohexanol (e.g., bound can include cyclohexanol bound to adipic acid), propionic acid, butyric acid, valeric acid, caproic acid, propanol (e.g., 1-propanol and 2-propanol), butanol (e.g., 1-butanol, 2-butanol, etc.), pentanol (e.g., 1-pentanol, 2-pentanol, etc.), hexanol (e.g., 1-hexanol, 2-hexanol, etc.), and the like. Reference to "removing monofunctional components" monofunctional compounds, such as "removing free and bound monofunctional components" refers to removing from the mixture referred to, such as by heating and distillation, both free monofunctional components (e.g., monocarboxylic acids, mono-hydroxy compounds, and the like), and those products that can be derived from cleavage of bound monofunctional components under the conditions of removal (e.g., heat, vacuum, acid catalysis) to yield free monofunctional components in the course of the process step, which are then removed by distillation or the like along with the free monofunctional components.

A "polyfunctional" or "polyfunctional compound", as used herein, refers to compounds that have more than a single functional group capable of forming new bonds under the conditions of heating and, optionally, catalysis as disclosed herein. Examples include diacids, diols, hydroxyacids, hydroxyesters, and the like.

Pressures reported as pounds per square inch gauge (psig) are relative to one atmosphere. 1 pound per square inch=6.895 kilopascal. One atmosphere is equivalent to 101.325 kilopascals, and one atmosphere is about 14.7 pounds per square inch absolute (psia) or about 0 pounds per square inch gauge (psig).

The term "about" as used herein, when referring to a numerical value or range, allows for a degree of variability in the value or range, for example, within 10%, or within 5% of a stated value or of a stated limit of a range.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

Byproduct Mixtures Water Wash, COP Acid, and Non-Volatile Residue

Available cyclohexane oxidation process byproduct streams include "Water Wash" (the aqueous stream produced by water extraction of cyclohexane oxidate); "COP Acid", a concentrate of Water Wash produced by removal of at least some of the water; and Non-Volatile Residue "NVR" (the high-boiling distillation bottoms from distillative recovery of main process products cyclohexanol and cyclohexanone). These byproduct streams can be converted to polyol compositions of the invention as described and claimed herein, which can then be used, e.g., in the production of polyurethane and polyisocyanurate polymers of the invention via pre-polymer compositions of the invention, said polymers and their precursor pre-polymer compositions being useful in the various products such as coatings, binders, and the like, as disclosed and claimed herein.

The byproduct mixture that is processed via the inventive methods herein to provide the polyol composition of the invention can be derived from one or a combination of Water Wash, COP acid, NVR, or a combination thereof. By "a combination thereof", is meant any one or a combination of two (Water Wash and COP acid; Water Wash and NVR; or COP and NVR) or a combination of all three (Water Wash, COP acid, and NVR). COP Acid may be provided by contacting cyclohexane air oxidation products with water in an extraction step and separating the Water Wash aqueous phase, followed by concentration by evaporation or the like. The Water Wash can be thermally treated to destroy peroxides that may pose difficulties during storage and shipment. The Water Wash can be concentrated by partial removal of water to reduce storage volume and transportation cost.

Wash Water can contain about 70% to 90% by weight water, e.g., about 85% by weight water. COP Acid generally can contain about 10% to 70% by weight water, e.g., about 10% to 50% by weight water. NVR can contain about 10% to 50% by weight water.

Water Wash, COP Acid, or NVR, or a combination thereof, can include monofunctional and polyfunctional byproducts of the cyclohexane oxidation reaction or process, in free and/or bound form. By "free form" is meant that the monofunctional compounds are not bound covalently to other compounds through bonds (e.g., ester bonds) subject to cleavage in the heating and distillation process, optionally in the presence of a transesterification catalyst. By "bound form" is meant that the monofunctional compounds are bound by covalent bonds subject to cleavage in the heating and distillation process (e.g., ester bonds), optionally in the presence of a transesterification catalyst. In the heating process, free monofunctional compounds present in the byproduct mixture can distill out of the mixture. Bound monofunctional compounds can undergo hydrolysis or transesterification, liberating the free form of the monofunctional compounds, which then can also be removed from the mixture by distillation.

The types of functional group(s) present in the organic components of the compounds present in a byproduct mixture of a cyclohexane oxidation reaction can include: an acid (e.g., a monobasic carboxylic acid and a dibasic carboxylic acid), a peroxide (e.g., a hydroperoxide, a dialkyl peroxide), a ketone (e.g., an aliphatic or cycloaliphatic ketone), an alcohol (e.g., an aliphatic alcohol, a cycloaliphatic alcohol), an ester (e.g., an aliphatic ester, a cycloaliphatic ester), an aldehyde (e.g., an aliphatic aldehyde, aldehyde-acid), a lactone (e.g., an aliphatic lactone), and an alkene (e.g., a keto-alkene, an alkene acid, an alkene alcohol); or a combination of the same or different functional groups in a single molecule (e.g., a hydroxyacid, a di-acid, a keto-acid, an aldehyde-acid, a diol, or an acid-hydroperoxide).

For example, in the byproduct mixture, prior to heat treatment, monoacids (monofunctional compounds) can include: formic acid, acetic acid, propionic acid, butyric acid, valeric acid, caproic acid, and the like. These can be present in free form, or in bound form as formates, acetates, propionates, and similar esters with hydroxy compounds. Diacids can include malonic acid, succinic acid, glutaric acid, adipic acid, fumaric acid, maleic acid, oxalic acid, hex-2-enedioic acid, and the like. These can be present in free or in bound forms also, but are not removed by distillation to any significant extent in the step of heating. Peroxides can include cyclohexylhydroperoxide, hydroxycaproic hydroperoxide, and the like. Ketones can include cyclohexanone, cyclopentanone, and the like.

Keto-acids can include an alpha-keto acid (e.g., a 2-oxo acid such as pyruvic acid), a beta-keto acid (e.g., a 3-oxo acid such as acetoacetic acid), a gamma-keto acid (e.g., a 4-oxo acid such as levulinic acid), a 5-oxo caproic acid, and the like. Keto-acids containing only one carboxylic acid group and no hydroxyl groups, such as the above examples, are considered monofunctional compounds herein, and can be removed during the heating/distillation process.

In the byproduct mixture, prior to heat treatment, monofunctional alcohols can include cyclohexanol, propanol (e.g., 1-propanol and 2-propanol), butanol (e.g., 1-butanol, 2-butanol, etc.), pentanol (e.g., 1-pentanol, 2-pentanol, etc.), hexanol (e.g., 1-hexanol, 2-hexanol, etc.). These can be present in free form, and can also be present in bound form, e.g., in combination with carboxylic acid groups as esters thereof. In the byproduct mixture, diols can include, 1,2-, 1,3-, and 1,4-cyclohexanediols, a butanediol isomer, a pentanediol isomer, and the like.

The components of the byproduct streams Water Wash, COP acid, and NVR can include monofunctional compounds, both free and bound, and polyfunctional compounds, including alcohols, carboxylic acids, and other types of functional compounds such as ketones, aldehydes, peroxides, and other oxygenates. The alcohols may form ester and/or polyester linkages with an acid functional group present in Water Wash, COP Acid, NVR, or a combination thereof. When the carboxylic acid is a mono-carboxylic acid, or the alcohol is a mono-ol, the acid or alcohol moiety respectively is a bound monofunctional, that can be liberated and removed during the step of heating and distillation, optionally in the presence of an catalyst such as an acid or an organometallic compound. When the carboxylic acid is a diacid, or the alcohol is a diol, the polyfunctional compounds can become incorporated into the polyol composition of the invention. For components of the byproduct mixture that have two different reactive functional groups, these can also become incorporated into the polyol composition of the invention by the processing steps disclosed and claimed herein. For example, a hydroxyacid can form ester or polyester linkages with themselves or with other polyfunctional materials present in the mixture.

More specifically, adipic acid can form an ester linkage (e.g., condensation reaction product) with the alcohol function in hydroxycaproic acid. In an embodiment, hydroxycaproic acid may form an ester linkage (e.g., condensation reaction product) with the alcohol function in another hydroxycaproic acid. Then, such diesters can themselves undergo transesterification with removal of monofunctional alcohols and formation of esters with polyhydroxy components like glycols.

A hydroxyacid can include hydroxycaproic acid, hydroxyvaleric acid, hydroxybutryic acid, hydroxypropionic acid, or hydroxyacetic acid. In an embodiment, the acid functional group is at one end of a linear chain (e.g., a hydrocarbyl chain) and the hydroxy group may be present in various positions along the chain. The hydroxycaproic acid can include 2-hydroxy-caproic acid, 3-hydroxycaproic acid, 4-hydroxycaproic acid, 5-hydroxy-caproic acid, and 6-hydroxycaproic acid, in which the hydroxyl group can be free, or can be bonded to a bound monoacid, or a bound polyacid. The hydroxyvaleric acid can include 2-hydroxyvaleric acid, 3-hydroxyvaleric acid, 4-hydroxyvaleric acid, and 5-hydroxyvaleric acid. The hydroxybutyric acid can include 2-hydroxybutyric acid, 3-hydroxybutyric acid, and 4-hydroxybutyric acid. The hydroxypropionic acid can include 2-hydroxypropionic acid and 3-hydroxypropionic acid.

Byproduct mixtures from two or more different reaction, e.g., one from adipic acid production and the other from caprolactam production, can be combined into a single byproduct mixture, which can be further processed into a polyol composition of the invention.

Polyol Methods and Compositions

The process of heating, optionally in the presence of a catalyst such as a transesterification or hydrolysis catalyst, has been found by the inventors herein to bring about rearrangement among the various free and bound forms of compounds present in the byproduct mixture, in particular, of carboyxlic acid and their esters, and hydroxy compounds (alcohols) and their esters. Bonds are broken and formed, and, it has been unexpectedly discovered that with removal of monofunctional compounds by distillation, the product remaining can comprise a polyol composition of the invention, useful for preparation of polyurethane (PU) and polyisocyanurate (PIR) polymers for various applications. When this transesterification and removal of monofunctional components is carried out in the presence of a polyhydroxy compound, e.g., a glycol, a triol, a tetraol, or a higher polyol, the resulting composition has been found by the inventors herein to have favorably low acid numbers and favorably high OH values to serve as polyol compositions suitable for, inter alia, the preparation of pre-polymer compositions with polyisocyanates, which mutually react and polymerize to form polyurethane and polyisocyanurate polymers of the invention.

Accordingly, the invention can provide a method of preparing a polyol composition, the method comprising:
heating a byproduct mixture comprising:
i) a water extract of a cyclohexane oxidation reaction product, optionally concentrated; or, ii) a non-volatile residue of a cyclohexane oxidation reaction product, optionally concentrated; or a mixture thereof,
and, one or more polyhydroxy compound, and optionally, a catalyst;
optionally under vacuum, or optionally with an inert gas sparge;
to remove monofunctional components and water by distillation.

A method of the invention can also further comprise a step of heating the byproduct mixture, optionally under vacuum, or optionally with an inert gas sparge, to remove monofunctional components and water, prior to adding the one or more polyhydroxy compounds, then, after adding the one or more polyhydroxy compounds, continuing to heat the resulting mixture. When this additional step of heating and distilling, optionally in the presence of a catalyst such as is suitable for transesterification reactions, prior to addition of the polyhydroxy compound takes place, it is believed that ester formation and transesterification takes place between the polyfunctional components of the byproduct mixture, as the monofunctional components are removed by distillation. Then, upon addition of the polyhydroxy compound, e.g., a glycol, triol, etc., and further heating, optionally in the presence of the same catalyst or another catalyst, further esterification and transesterification takes place along with distillative removal of monofunctional components along with water. The amount of polyhydroxy compound used can be about 3% to 50% by weight. Removal of water and monofunctionals can help drive the formation of esters from polyfunctional acids present in the byproduct mixture and the added polyhydroxy compounds.

The heating and distillation process following addition of the polyhydroxy component can continue for any suitable period to accomplish removal of water and monofunctional components, for example, the distillation process can continue until a remaining content of the monofunctional compounds, following the step of heating and removal thereof by distillation, is about 10% or less, or is about 5% or less, or is about 2% or less, by weight, of the composition. For some end uses, a more complete removal of monofunctionals can be favored, whereas for other end uses, the removal need not be as stringent. This can be determined by the end-user for the specific application.

Addition of a catalyst, or of more than a single catalyst, can facilitate the esterification and particularly the transesterification of the various carboxylic acid and hydroxylated components of the byproduct mixture and of the added polyhydroxy compound. As is well known in the art, catalysts reduce the activation barrier for a reaction to occur and, in conjunction with heating and distillative removal of water and monofunctional components, the presence of a catalyst can more quickly and effectively enable the reaction mixture to reach a favorable condition of condensation of its polyfunctional components to provide a polyol composition of suitable properties for the desired use. The catalyst can be a transesterification or a hydrolysis catalyst such as an acid or an organometallic compound, as is discussed in greater detail below.

A polyol composition of the invention can be made by removing water and monofunctional compounds from a byproduct mixture, such as described above. In an embodiment, the process includes heating (e.g., at about 100 to 300° C., or at about 150° C. to 250° C., or at about 180° C. to 200° C., or at about 235° C.) a mixture of functional monomers from one or more of the following: a water extract (Water Wash), a concentrated water extract (COP Acid), and a non-volatile residue (NVR), or a mixture thereof, and removing monofunctional components and, optionally, water, to form the inventive polyol composition. In an embodiment, heating is used in combination with vacuum (e.g. 10-400 mm Hg, or 40-300 mm Hg, or 300 mm Hg, or 50 mm Hg). In an embodiment heating is used in combination with sparging, or introduction of a gaseous substance beneath the liquid surface of the mixture to enhance removal of water and monofunctional compounds (e.g. an inert gas such as nitrogen, or superheated steam).

The monofunctional compounds and any associated water can be removed using the process (or system) such as distillation, a vapor-liquid separation (e.g., single-stage flash separation, evaporation (short-path, wiped, falling film, atmospheric, sub-atmospheric), a multi-stage distillation, multiple instances of these, or combinations of these), a liquid-liquid separation by differential solubility, a solid-liquid separations (e.g., fractional crystallization), separation by molecular size and shape (e.g., membrane separation), post treatments (e.g., carbon decolorizing, clay treatments, and the like), and combinations of each of these (e.g., extractive distillation, distillation followed by post treatments, and the like).

The polyhydroxy component can be selected for production of a polyol composition based upon the desired properties of the polyol composition. Any suitable polyhydroxy compound can be used; for example, the polyhydroxy compound can be a dihydroxy compound (diol), trihydroxy compound (triol), a tetrahydroxy compound (tetraol), or a higher polyhydroxy compound. More specifically, the polyhydroxy compound can be ethylene glycol, diethylene glycol, polyethylene glycol, propylene glycol, dipropylene glycol, polypropylene glycol, butanediol, pentanediol, hexanediol, glycerine, trimethylolpropane, pentaerythritol, or sorbitol, or a combination thereof.

While not wishing to be bound by theory, it is believed that polyols suitable for use as a component of a PU or PIR polymer can arise through transesterification of, e.g., methyl esters of compounds such as the adipoylhydroxycaproate with the polyhydroxy compounds, such as by a process exemplified with diethyleneglycol, shown below in Scheme 1, wherein the R group is either hydrogen or is a monovalent organic radical, e.g., cyclohexyl, that yields a monofunctional alcohol, ROH, e.g., cyclohexanol, on hydrolysis. Byproduct monofunctional alcohols, e.g., cyclohexanol, is removed, e.g., by distillation. This reaction is illustrative of the sorts of reactions that can occur under conditions of esterification and transesterification, optionally in the presence of a suitable catalyst, under conditions of heating and distillative removal of water and monofunctional components.

When R is other than hydrogen, Scheme 1 shows an example of a monofunctional hydroxy compound ROH bound to a polyfunctional carboxylic acid in reaction with diethylene glycol, that is, a transesterification reaction yielding a bis(diethyleneglycol) ester of the dicarboxylic acid.

Related reactions involving other monofunctional compounds such as monoacids such as shown in Scheme 2. Scheme 2 illustrates displacement of a bound monofunctional carboxylic acid (valeric acid) by a polycarboxylic acid (adipic acid), following which the liberated valeric acid can be removed by distillation and the remaining adipoyl hydroxycaproate reacted with diethyleneglycol to form a polyol polyester, water of esterification (not illustrated) being removed by distillation.

Under the conditions of heating and removal of monofunctional components, optionally in the presence of a catalyst suitable for catalyzing esterification and transesterification, removal of the monofunctional components, e.g., monofunctional acids and alcohols, results in the equilibriums being driven towards formation of esters between only polyfunctional components. Added polyhydroxy compounds, such as glycols, further enter into this set of reactions, such that carboxylic acids become esterified with at least one hydroxyl group of a polyhydroxy compound. For example, in when a glycol is used, one hydroxyl group can become esterified with a carboxylic acid group from a polyfunctional acid, and the other hydroxyl group can remain unesterified, thus resulting in a composition containing hydroxyl groups and comprising ester bonds. Such hydroxyl groups are then available for reaction with isocyanates to form urethane bonds in PU and PR polymers.

Scheme 1: Formation of an Ester of Polyfunctional Alcohol Diethylene Glycol

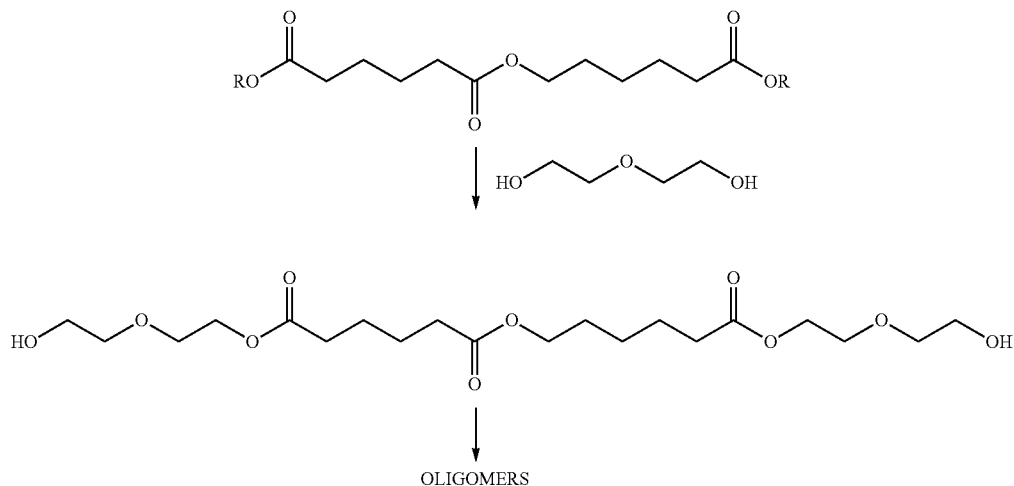

OLIGOMERS

In the above example, when R is H, the reaction of the diethylene glycol with the dicarboxylic acid is an esterification, and water is released, which can be removed by distillation. When R is a group such as an alkyl group or a cycloalkyl group, the reaction with diethylene glycol is a transesterification, and the monofunctional alcohol, e.g., cyclohexanol, is released and then removed by distillation.

Scheme 2: Transesterification of an Ester of Monofunctional Pentanoic Acid to an Ester of Polyfunctional Adipic Acid, Followed by Esterification with Diethylene Glycol

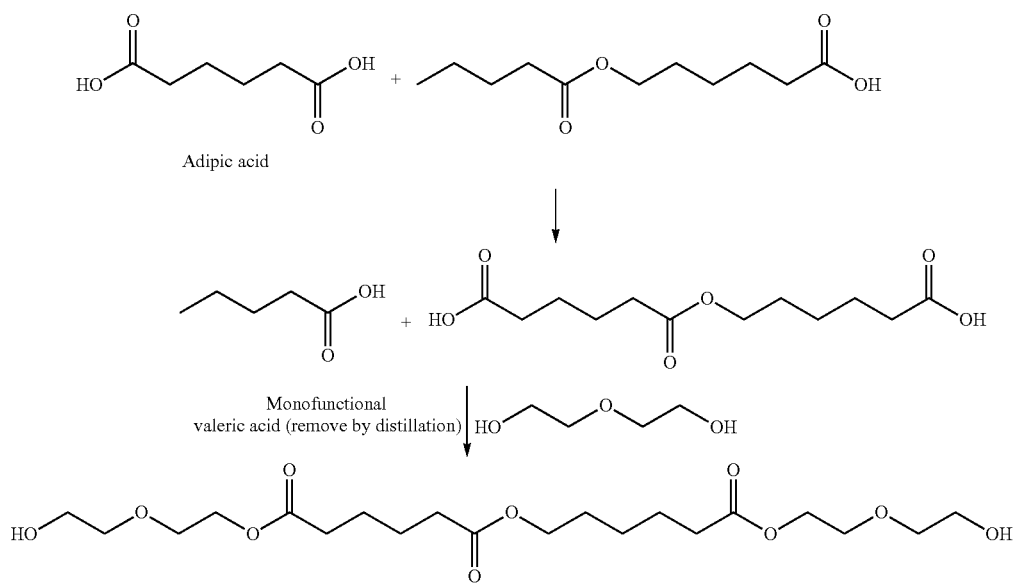

Thus, one polyol produced by a method of the invention is a dihydroxy-triester, which can be categorized as a polyol-polyester. As is apparent to the practitioner, further transesterification steps can take place to provide mixed oligomers of higher molecular weight. Other difunctional, trifunctional, and higher polyfunctional esters, remaining in the byproduct mixture after removal of the monofunctional components, can likewise undergo transesterification reactions with the various polyhydroxy compounds as disclosed and claimed herein to provide various species of polyol-polyester, useful for condensation with diisocyanates, triisocyanates, and higher polyisocyanates to provide PU and PIR polymers of the invention, as further described below. The removal of monofunctional components decreases the concentration of chain terminating moieties in the mixture being heated; for example, bound monofunctional components like esters of monofunctional alcohols or of monofunctional carboxylic acids would serve to eliminate a reactive group on a molecular terminus, because such esters do not include further functionality that could react, e.g., with isocyanates, to form carbamate (urethane) bonds. However, by displacing and removing monofunctional compounds from the milieu, esterification can take place with a difunctional or trifunctional, or higher polyfunctional compound (glycols, polycarboxylic compounds, hydroxyesters, etc), forming esters that have further functionality that will be available for urethane bond formation in a subsequent process to form a polyurethane polymer. Thus, removal of monofunctional components can serve to increase chain length and available reactive functionality of the polyol compositions of the invention.

A third component comprising a polyfunctional acid, or an activated ester thereof, or a polyfunctional ester or an anhydride thereof, or a combination thereof, can be added to the mixture, whereupon monofunctional components can be removed by distillation, to a level of 10% or less, or 5% or less, or 2% or less on a weight basis. By a "polyfunctional acid" is meant a carboxylic acid having two or more carboxylate groups. By an "activated ester thereof" is meaning an ester of a polyfunctional acid that can undergo transesterification or hydrolysis under the conditions of heating of the byproduct mixture. By a "polyfunctional ester thereof" is meant an ester of the polyfunctional carboxylic acid with one or more polyfunctional alcohols, such as a glycol ester. By an "anhydride thereof" is meant an intramolecular or intermolecular anhydride of one or two, respectively, polycarboxylic acids as defined above.

For instance, the third component can comprise, or can be, a polyfunctional aromatic acid, or an anhydride thereof, or an activated ester thereof, or a polyfunctional ester thereof, or a mixture thereof. More specifically, the polyfunctional aromatic acid, the activated ester thereof, the polyfunctional ester thereof, or the anhydride thereof, can comprise, or can be, terephthalic acid, isophthalic acid, orthophthalic acid, trimellitic acid, pyromellitic acid, or any combination thereof. The amount of third component used can be about 1%-30% by weight.

For instance, the third component can comprise, or can be, a polyfunctional aliphatic acid, or an activated ester thereof, or a polyfunctional ester thereof, or an anhydride thereof; or a mixture thereof. More specifically, the third component can comprise, or can be, glycolic acid, citric acid, lactic acid, malic acid, fumaric acid, maleic acid, succinic acid, glutaric acid, or adipic acid; or an activated ester thereof; or a polyfunctional ester thereof; or an anhydride thereof; or a mixture thereof. The amount of third component used can be about 1%-30% by weight.

The selection of the identity of the third component comprising a polyfunctional carboxylic acid can impact the properties of products using the polyol composition of the invention. For instance, as described below, polyurethane polymers comprising an aromatic acid or derivative thereof in the polyol component prepared as described above, when used as a coating of a particulate fertilizer, can provide a more favorable, i.e., prolonged, period of fertilizer release after application to soil, compared to polyurethane polymers that do not comprise an aromatic acid or derivative thereof, under comparable conditions.

In preparing a polyol composition of the invention a polyfunctional crosslinker or chain extender with two or more reactive hydroxyl or amino functionalities can be added during the heating/distillation stage. For example, the polyfunctional crosslinker or chain extender can be ethylene glycol, diethylene glycol, triethylene glycol, propylene glycol, dipropylene glycol, tripropylene glycol, 1,3-propanediol, 1,3-butanediol, 1,4-butanediol, 1,6-hexanediol, cyclohexane dimethanol, hydroquinone bis(2-hydroxyethyl)ether, neopentyl glycol, glycerol mono-oleate, ethanolamine, diethanolamine, triethanolamine, methyl diethanolamine, phenyl diethanolamine, trimethylolpropane, 1,2,6-hexanetriol, pentaerythritol, N,N,N',N'-tetrakis-(2-hydroxypropyl)ethylenediamine, diethyltoluenediamine, or dimethylthiotoluenediamine; or any mixture thereof.

More specifically, the polyfunctional crosslinker or chain extender can have three or more reactive hydroxyl or amino functionalities; for example, the polyfunctional crosslinker or chain extender can be glycerol, triethanolamine, trimethylolpropane, 1,2,6-hexanetriol, pentaerythritol, or N,N,N',N'-tetrakis-(2-hydroxypropyl)ethylenediamine; or any mixture thereof.

In practicing a method of the invention, use of a catalyst, such as a transesterification catalyst, can increase the rate and completeness of the reactions involved in producing the polyol composition. For example, the catalyst can be an acid, e.g., toluenesulfonic acid or xylenesulfonic acid; or the catalyst can be a carboxylate salt, e.g., potassium acetate or potassium octoate; or the catalyst can comprise an organometallic compound, e.g., an organomercury, organolead, organoferric, organotin, organobismuth, or organozinc compound. More specifically, the organometallic compound can be tetraisopropyl titanate or dibutyl tin dilaurate, well known as effective transesterification catalysts. The specific catalyst and concentration used are determined by methods known to those skilled in the art. The catalyst is typically about 0.01 to 1% by weight of the resin blend composition, but may be higher or lower as required according to catalyst activity.

An additional component that can be added to the byproduct mixture can include a hydrophobic material, the addition of which can be followed by heating and removing monofunctional components by distillation. Use of a hydrophobic material in preparation of a polyol composition of the invention can modify the properties, e.g., of polyurethane polymers subsequently prepared by using the inventive polyol composition as a polyol component in conjunction with a polyisocyanate in formation of the polyurethane polymer. For example, the hydrophobic material can comprise a natural oil, a fatty acid or a fatty acid ester derived therefrom; or a mixture thereof. More specifically, the hydrophobic material can comprise a plant oil, a fatty acid or a fatty acid ester derived therefrom; or a mixture thereof. Or, the hydrophobic material comprises an animal oil, a fatty acid or a fatty acid ester derived therefrom, and mixtures thereof. Specifically, the hydrophobic material can comprise one or more of tallow oil, tall oil fatty acid, soybean oil, coconut oil, castor oil, linseed oil, a nonedibile plant-derived oil, or an edible plant-derived oil. Alternatively, the hydrophobic material can comprise a synthetic oil, a synthetic fatty acid, or a synthetic fatty ester. Or, the hydrophobic material can be an aminated material, a hydroxylated material, or a combination thereof, such as an amine, an aminoalcohol, a hydroxyacid, or a combination thereof.

Optionally, one or more additional ingredient can be added, selected from the group consisting of another polyol, a solvent, a catalyst, a chain extender, a crosslinking agent, a curative, a surfactant, a blowing agent, a filler, a flame retardant, a plasticizer, a light stabilizer, a colorant, a wax, a biocide, a mineral, a micronutrient, an inhibitor, a stabilizer, or an organic and inorganic additive.

In preparation of a polyol composition of the invention, components can be added and the mixture further processed, e.g., by heating and distillation of monofunctional components, until favorable properties of the product are achieved. For example, a polyol composition with favorable properties for preparation of PU/PIR polymers has a relatively low free carboxylic acid content (which can be expressed as acid number, defined above). More specifically, a polyol composition suitable for preparation of a PU/PRI polymer can have an OH value of about 100 to 500 mg KOH/gm of sample; or, can have an acid number of less than 10 mg KOH/gm of sample, or less than 5 mg KOH/gm of sample, or preferably less than 1 mg KOH/gm of sample; or any combination thereof. A polyol with a low acid number, such as less than 10 mg KOH/gm of sample, or less than 5 mg KOH/gm of sample, or preferably less than 1 mg KOH/gm of sample, has relatively few free, un-esterified carboxylic acid groups. A polyol with a high OH value, such as about 100 to 500 mg KOH/gm of sample, has a relatively high proportion per mass of reactive hydroxyl groups available for condensation with isocyanate groups of the polyfunctional isocyanate to yield the urethane (carbamate) groups of a resulting PU or PR polymer.

Accordingly, the invention can provide a polyol composition prepared using any combination or subcombination of the above-recited methods and variants thereof. As described below, these polyol compositions find uses in many final products, thus conferring a higher value on what has hitherto been a waste product of a chemical process.

Resin Blends and Pre-polymer Compositions for Forming PU and PIR Polymer Compositions The present invention can provide resin blend compositions for foamed and non-foamed applications that include polyol compositions of the invention as components. Embodiments of the resin blend include a polyester polyol prepared as described herein, and additionally one or more other components, such as catalysts and modifiers, known to those skilled in the art and dependent on end use. Such components may include, in addition to catalysts for the reaction, other modifier polyols, solvents, chain extenders, crosslinking agents, curatives, surfactants, blowing agents, fillers, flame retardants, plasticizers, light stabilizers, colorants, waxes, biocides, inhibitors, stabilizers, minerals, micronutrients, or other organic or inorganic additives. A resin blend can be a composition of sufficient stability to be shipped, or stored for prolonged periods, while retaining its reactivity with an intended coreactant sufficient to form a pre-polymer and polymer having properties adequate for the intended function. A resin blend can contain a coreactant, provided that the coreactant component and the polyol component of the resin blend react at a sufficiently low rate for the purpose intended.

A resin blend can comprise a polyol prepared as described herein and one or more of the aforementioned components, and can exclude coreactive ingredients such as polyisocyanates. Resin blends excluding coreactive ingredients have longer shelf life than resin blends containing such ingredients and may be blended with coreactive ingredients such as isocyanate at the time of use. However, a resin bland can, in some specific circumstance under conditions wherein premature reaction is not an issue, also include a coreactant. Typically, however, a resin blend does not contain a coreactant until a coreactant, e.g., a polyisocyanate, suitable for preparation of a pre-polymer composition and resulting polymer, e.g., a polyurethane, is added at the time of use.

A "pre-polymer composition" refers to a composition that can be semi-liquid or flowable prior to the mutual reaction of the polyol component and the coreactant, and can be obtained by mixing the two mutually reactive components, that upon reaction can "set up" to form a solid polymer material. For example, a polyurethane-forming pre-polymer composition can include a polyol composition or a resin blend of the invention, plus a polyfunctional isocyanate as a coreactant, and other optional ingredients such as catalysts, as outlined above. Before mutual reaction of the polyol composition and the coreactant, such as the "B-side" polyfunctional isocyanate, the physical state of the pre-polymer composition can be liquid or quasi-liquid, having a viscosity depending upon specific components, or can be a malleable soft gel. As reaction occurs between the polyol composition of the invention and the reactive, e.g., isocyanate, groups of the coreactant, the hydroxyl groups of the polyol can react with the isocyanate groups to form carbamate (urethane) bonds. To the extent that modifiers and the like containing amino groups are present in the resin blend, reaction with the isocyanate groups can yield urea groups as well. As this covalent reaction proceeds in the pre-polymer composition, the physical state of the substance changes from the liquid or quasi-liquid state to a solid state, in which the polymeric product is present. When the pre-polymer composition solidifies into the solid polymer product, it is said that the material "sets" or "sets up." If a solvent is present in the pre-polymer composition, the solvent can at least partially evaporate during the condensation or "setting up" process.

By this means, application of a pre-polymer composition as a coating, adhesive, sealer, binder, and the like, to an object or objects, can be accomplished while the pre-polymer composition is flowable, sprayable, or spreadable, but on standing for a suitable period of time, such as minutes to hours, and at a suitable temperature, such as room temperature or higher (or in certain combinations, below room temperature), the mixture undergoes polymerization/cross-linking, and a solid, if flexible, material is produced. By room temperature is meant a temperature in the range of about 20° C. to 25° C. Alternatively, the coating, adhesive, sealer, binder, and the like, can be applied to the object or objects by separately applying the resin blend and the coreactant, either simultaneously or sequentially, such that the pre-polymer composition is formed in situ on the surface(s) of the object(s).

It is understood that the polyurethane or polyisocyanurate polymer that results can still have a tacky texture, and can still contain residues of optional solvents and the like, but a phase transition from liquid to solid has taken place. The solid material then provides the coating or sealing effect, and, if adherent to the object(s), the adhesive effect.

The liquid or quasi-liquid pre-polymer composition can be foamed by use of a blowing agent, i.e., a volatile material that liquefies and expands within the solidifying pre-polymer composition, producing bubbles in the material, that are then present in the final foam structure containing the solid polymer reaction product. Foams can be adherent as well, depending upon the nature of the objects they contact, and can be used as insulation, packing, and the like. Or, the foam can set up without adherence, producing solid foam blocks, sheets, packing peanuts, and the like.

A pre-polymer composition comprising a polyol composition of the invention and a polyfunctional isocyanate can yield a polyurethane polymer, or a polyisocyanurate polymer, or a polymer that can include both functional groups, depending on the conditions and the ratios of reactants present in the blend, as is known in the art. The polyurethane polymer contain predominantly carbamate groups of formula R—NH—C(═O)—O—R', wherein R and the bonded nitrogen-carbonyl is derived from the isocyanate coreactant, and R'—O is derived from the polyol, with the understanding that R and R' have other functional groups bonded thereto that themselves are further bonded, providing the high molecular weight polymer substance. A polyisocyanurate polymer contains triazine rings in addition to the urethane bonds, which are believed to be formed via the reaction of three of the diisocyanate molecules to yield an intermediate of formula

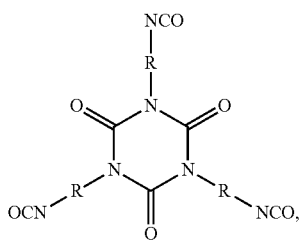

which can then react at the exocyclic isocyanate groups with polyol hydroxy groups to yield the PIR polymer, a variant of the PU polymer. Thus, PR polymers can be more highly crosslinked, and more rigid, than some PU polymers, although both kinds of polymers do contain domains of linear polyurethane. It is known to use various amines and polyamines as curatives, crosslinkers, or chain extenders and it should be understood that when primary or secondary amines are used as such that urea linkages may be present in the resulting polymer. Urea linkages have the structure R—NH—C(═O)—NR'R", wherein R and the bonded nitrogen-carbonyl is derived from the isocyanate coreactant, and —NR'R" is derived from the primary or secondary amine, with the understanding that either R' or R" but not both may be H and R, R', and R" have other functional groups bonded thereto that themselves are further bonded, providing the high molecular weight polymer substance.

It is known in the art that use of higher relative amounts of coreactant isocyanates, such as MDI, and use of polyester polyols, such as the polyol compositions of the present invention, can favor formation of polyisocyanurate linking groups over carbamate linking groups.

Accordingly, the invention can provide a pre-polymer composition for formation of a polymer, comprising a polyol of the invention, a coreactant, and optionally, a catalyst, and optionally, a solvent. For example, the coreactant can be a polyfunctional isocyanate, for formation of a PU or PR polymer.

A pre-polymer composition can include the polyester polyol of the invention, a coreactant such as a diisocyanate, and optionally a catalyst for non-foamed applications such as polyurethane based coatings, binders, adhesives, sealants, and elastomers. The pre-polymer composition can include the polyol composition, a coreactant, and a catalyst for coating applications. Other components can be included; for example, a solvent can be used for coating applications. The pre-polymer composition including a polyol composition of the current invention can also include any one or combination of polyurethane formulation components known to those skilled in the art, such as described in the book "Polyurethanes Chemistry, Technology, and Applications by Z. Wirpsza (Ellis Horwood, 1993).

Accordingly, the present invention can provide methods and compositions for a polyurethane polymer, the method of preparation comprising mixing a polyol composition of the invention, or a polyol composition prepared by the method of the invention, and a polyfunctional isocyanate. A polyfunctional isocyanate is an isocyanate with at least 2 isocyanate functional groups per molecule. For example, the polyfunctional isocyanate can comprise, or can be, monomeric methylene diphenyl diisocyanate (MDI), polymeric MDI, an aliphatic diisocyanate, a cycloaliphatic diisocyanate, an aromatic diisocyanate, a multifunctional aromatic isocyanate, an organic polyisocyanate, a modified polyisocyanate, an isocyanate-based prepolymer, or a mixture thereof. More specifically, the polyfunctional isocyanate can include more than two isocyanate groups, on average, per molecule. For example, the polyfunctional isocyanate can be polymeric MDI (PMDI) with average functionality of about 2.1 to about 3.3.

A catalyst can be added when mixing the polyol composition and the polyfunctional isocyanate. For example, the catalyst can comprise an amine, e.g., triethanolamine or diazobicyclooctane; or the catalyst can comprise an organometallic compound such as tetraisopropyl titanate or dibutyl tin dilaurate; or the catalyst can comprise a metal carboxylate, such as potassium acetate or potassium octoate.

Depending on the use of the PU or PIR polymer, a solvent can be added when mixing the resin blend and the polyfunctional isocyanate. For example, solvent can comprise a hydrocarbon, such as toluene.

Similarly, the invention can provide a method of preparing a polyisocyanurate polymer, comprising mixing a resin composition of the invention, or a resin composition prepared by the method of invention, and MDI. The method can further comprise adding a catalyst, such as an amine like triethanolamine or diazobicyclooctane (e.g., a DABCO® series catalyst from Air Products Corp.), when mixing the resin composition and the MDI.

Examples of PU/PIR polymers made using the inventive polyol compositions are described in more detail in the Examples, below.

The invention can provide foam compositions, comprising a resin blend of the invention or prepared by a method of the invention, and a polyfunctional isocyanate, with a blowing agent. The foam composition incorporating a polyester polyol resin of the invention or prepared by a method of the invention can be used in rigid applications such as in appliance, spray, and other pour-in-place applications. The foam composition incorporating a polyester polyol blend resin of the invention or prepared by a method of the invention can be used in flexible applications as in slabstock or moulded foams for automotive applications, furniture/bedding cushioning applications, packaging applications, etc The pre-polymer composition for producing a PU or PIR polymer can include an inventive polyol composition or resin blend, and a coreactant such as a diisocyanate or a polyisocyanate can also include a surfactant, a catalyst, and a blowing agent for foamed applications.

The surfactant for use in foamed applications includes any surfactant known to a skilled person in the art for the purposes of making a suitable PU and/or PIR spray foam. In an embodiment, the surfactant can include silicone based surfactants, organic based surfactants, and a mixture thereof. In an embodiment, the surfactant is about 0.25 to 3.0% by weight of the pre-polymer composition.

Accordingly, the invention can provide a foam composition comprising a polyurethane polymer of the invention or prepared by the method of the invention, or a polyisocyanurate polymer of the invention or prepared by the method of the invention, and a blowing agent, and, optionally, a surfactant. As described above, the foam comprising the polymer can be formed by foaming a liquid or quasi-liquid pre-polymer composition that is a precursor to the polymer, the pre-polymer composition components then setting up to yield the solid foam material. The blowing agent that creates the foam in, e.g., a viscous liquid pre-polymer composition, can be any suitable volatile material. For example, the blowing agent can comprise a hydrocarbon having 3 to 7 carbon atoms, a hydrofluorocarbon, water, carbon dioxide, or a mixture thereof. More specifically, a hydrofluorocarbon blowing agent can be 1,1,1,3,3-pentafluoropropane (HFC-245fa), 1,1,1,2-tetrafluoroethane (HCF-134a), 1,1-dichloro-1-fluoroethane (HCFC 141-B), chlorodifluoromethane (HCFC R-22), 1,1,1,3,3-pentafluorobutane (HFC-365mfc), or a combination thereof. More specifically, a hydrocarbon blowing agent can be butane, n-pentane, i-pentane, cyclopentane, hexane, cyclohexane, any of their alkene analogues, or a combination thereof.

Or, the blowing agent can include two or more blowing agents (e.g., blowing agent, co-blowing agent, and the like). For example, the blowing agent can be 1,1,1,3,3-pentafluoropropane and the co-blowing agent can be water, where 1,1,1,3,3-pentafluoropropane can be about 60 to 99% by weight of the blowing agents and water can be about 1 to 40% by weight of the blowing agents.

The total amount of the blowing agent(s) can be about 5 to 25% by weight or can be about 8 to 15% by weight, of the pre-polymer composition.

Thus, the invention can provide a method of preparing a foam composition, comprising mixing a polyol of the invention, a polyfunctional isocyanate, and a blowing agent, to yield a pre-polymer composition comprising the blowing agent, which foams and sets up to yield the foam formed of the solid polymer material. The mixture can be sprayed, foamed in place, or otherwise applied in any suitable manner where a foam is needed.

A catalyst can be used in preparing a foam composition of the invention. The catalyst can include a metal-based catalyst, amine-based catalyst, or a mixture thereof. The metal-based catalyst can include, but is not limited to, organomercury, organolead, organoferric, organotin, organobismuth, organozinc catalysts (e.g., stannous octoate and dibutyltin dilaurate), and a combination thereof. The amine-based catalyst can include, but is not limited to, triethylenediamine, N-methylmorpholine, pentamethyl diethylenetriamine, dimethylcyclohexylamine, tetramethylethylenediamine, 1-methyl-4-dimethylaminoethyl-piperazine, 3-methoxy-N-dimethylpropylamine, N-ethylmorpholine, diethylethanolamine, N-cocomorpholine, N,N-dimethyl-N',N'-dimethylisopropylpropylene diamine, N,N-diethyl-3-diethyl aminopropylamine, dimethyl-benzyl amine, triethanolamine, triisopropanolamine, or any combination thereof. The catalyst can be present at about 0.001 to 10% by weight of the pre-polymer composition.

In various uses, a pre-polymer composition comprising a polyol of the invention and a coreactant, such as a polyfunctional isocyanate, can include a solvent, e.g., for coating uses, adhesive uses, binder uses, and the like. In an embodiment a solvent can be one or more substances that are liquid at temperature of use and capable of dissolving the pre-polymer composition. Solvents may be non-reactive solvents that do not react with isocyanate, or reactive solvents that react with isocyanate and become incorporated into the polyurethane. Use of reactive solvents can help reduce emissions of volatile organic compounds (VOCs) during use of the pre-polymer composition. Suitable solvents may include but are not limited to toluene, xylene and other aromatic solvents including higher-boiling mixtures such as Aromatic 150 (e.g., Solvesso 150® of Exxon Mobil Chemical), limonene and other unsaturated hydrocarbons, ester solvents such as methyl acetate, ethyl acetate, propyl acetate, butyl acetate, t-butyl acetate, methyl glycolate, ethyl glycolate, propyl glycolate, butyl glycolate methyl lactate, ethyl lactate, propyl lactate, butyl lactate, dimethyl succinate, dimethyl glutarate, dimethyl adipate, diisobutyl succinate, diisobutyl glutarate, diisobutyl adipate, methyl 6-hydroxycaproate, methyl 5-hydroxyvalerate, methyl 4-hydroxybutyrate, methyl levulinate, ethyl levulinate, butyrolactone, valerolactone, 3-ethoxy ethyl propionate (EEP), esters derived from natural fats and oils such as methyl soyate, esters derived from other bio-based materials such as isosorbide esters or bio-succinic acid esters, carbonates such as dimethyl carbonate or propylene carbonate, ethers such as tetrahydrofuran and dimethyl isosorbide, ketones such as acetone, 2-butanone, methyl isobutyl ketone, diisobutyl ketone, and isophorone, amides such as dimethyl formamide (DMF) or dimethyl acetamide (DMAC), glycol ethers such as ethylene glycol butyl ether (EB), diethylene glycol butyl ether, and tripropylene glycol methyl ether, glycol esters such as ethylene glycol diacetate and propylene glycol diacetate, glycol ether esters such as propylene glycol methyl ether acetate, propylene glycol methyl ether propionate, dipropylene glycol methyl ether acetate, ethylene glycol butyl ether acetate, diethylene glycol butyl ether acetate, halogenated solvents such as methylene chloride and p-chlorobenzotrifluoride, and others including dimethyl sulfoxide (DMSO), N-methylpyrrolidone (NMP), etc, In the United States, certain solvents may be preferred over others because they are considered to be VOC exempt or because they have low photochemical reactivity. VOC exempt solvents are listed in the United States Code of Federal Regulations, Title 40, Part 51.100 and include, among others, acetone, methyl acetate, dimethyl carbonate, methylene chloride, t-butyl acetate, propylene carbonate, and p-chlorobenzotrifluoride. Low photochemical reactivity refers to the tendency of a solvent to participate in photochemical reactions that contribute to ground-level ozone and "smog." One measure of photochemical reactivity is maximum incremental reactivity (MIR) as described in work by Professor William P. L. Carter and others; see for example "Development of ozone reactivity scales for volatile organic compounds" by William P. L. Carter published in the Journal of the Air and Waste Management Association, volume 44, pages 881-899, Jan. 20, 1994. Dimethyl succinate and dimethyl glutarate are two examples of solvents having desirable low MIR values of 0.23 and 0.42 respectively.

The pre-polymer composition, e.g., for foamed applications, can be prepared by methods known by the skilled person. For example, resin blend compositions of the invention can be added to a blend tank and mixed under ambient conditions with the coreactant and catalyst, if used, and, if the blend tank is pressure rated, the blowing agent may be added last and all the compositions mixed for a period of time until a homogenous mixture is produced. When the composition is dispensed and the pressure released, foaming of the pre-polymer composition occurs to provide a foamed polymer upon set-up.

As mentioned above, embodiments of the present disclosure include compositions for coatings, adhesives, sealants, elastomers, and binders that include a reaction product of an inventive polyol composition or resin blend comprising the polyol, with a polyfunctional isocyanate. Embodiments of the present disclosure also include pour-in-place foam compositions, appliance foam compositions spray foam compositions, polyisocyanurate foam compositions that include a reaction product of the polyol composition with a polyfunctional isocyanate. The polyol composition can include any of the polyol compositions described herein.

For example, the polyfunctional isocyanate can include any isocyanate with an average functionality of at least two that can be used to make a suitable polyurethane and/or polyisocyanurate foam.

As noted above, the present disclosure can provide polymer foams including polyurethane and/or polyisocyanurate foams. The PU and/or PIR foam can include an aliphatic polyester polyol composition, a coreactant polyisocyanate, a catalyst, a surfactant, and a blowing agent. The aliphatic polyester polyol composition can include any of the aliphatic polyester polyol compositions described herein. In addition, the catalyst, the surfactant, and the blowing agent can be any of the catalyst, the surfactant, and the blowing agent described herein.

The pre-polymer composition can be used to produce a polyurethane and/or a polyisocyanurate foam for spray or other types of application with an NCO index ranging from about 100 to 400. In an embodiment, the aliphatic polyester polyol blend composition for this use can have an average functionality of at least about 1.5 and an overall hydroxyl value of at least about 120.

The PU and/or PR foam can be produced at various volume ratios of polyol composition and polyisocyanate to obtain a certain Isocyanate Index. The ratios are normally referred to as A:B where "A" (or A-side component) is the polyisocyanate and "B" (or B-side component) is the polyol composition, according to common usage in the USA, although A-side and B-side may have other meanings in other parts of the world (e.g., in Europe). In an embodiment, the ratio can be about 1:1 to 4:1.

The A-side component can be a polyisocyanate of the formulations disclosed herein which can incorporate polymeric MDI (PMDI). As those skilled in the art know, Mondur® MR Lite from Bayer Corporation and Rubinate® M from Huntsman Corporation are typically used. However, it is not intended the A-side component be limited to those specifically illustrated herein. For example, the A-side component of the formulations of the present disclosure can be selected from organic polyisocyanates, modified polyisocyanates, isocyanate-based prepolymers, and mixtures thereof. Such choices can also include aliphatic and cycloaliphatic isocyanates, but aromatic and especially multifunctional aromatic isocyanates are particularly useful.

The invention can also provide a sealant, adhesive, or binder, comprising a polyurethane polymer of the invention, or prepared by the method of the invention, or a polyisocyanurate polymer of the invention or prepared by the method of the invention. For example, the invention can provide a fiber-reinforced composite material comprising a polyurethane polymer of the invention or prepared by the method of the invention, or a polyisocyanurate polymer of the invention or prepared by the method of the invention; and a cellulosic substance. More specifically, the cellulosic substance can comprise wood fibers, as is described in more detail in the Examples, below. Pre-polymer compositions of the invention, comprising a polyol of the invention, a coreactant, and optionally, a catalyst, and optionally, a solvent are provided. Such pre-polymer compositions can be used as needed in various sealant and adhesive applications.

Pre-polymer compositions of the invention can also be used to coat fertilizers to provide PU/PIR polymer-coated particulate fertilizers that can have extended or controlled release properties under field conditions. Thus, the invention can provide a particulate fertilizer composition, comprising a fertilizer substance in particulate form, with a coating comprising a polyurethane polymer of the invention or prepared by the method of the invention, or a polyisocyanurate polymer of the invention or prepared by the method of the invention. The fertilizer substance incorporated therein can be urea, such as prilled urea or granular urea. As is shown in FIG. 1, and is discussed in greater detail below in the Examples, differing degrees of delay of fertilizer release under field conditions can be achieved using different coating formulations. For example, FIG. 1 indicates that PU compositions containing a higher content of aromatic groups, derived from the third component as described above, can achieve more prolonged periods of release than can PU compositions containing lower contents of aromatic groups. The coating, which can undergo decomposition by physical or by biological processes, or both, can be biodegradable.

A polymer coating can be applied to the particulate fertilizer material according to various methods that produce a pre-polymer coating on the fertilizer particles. For example, a resin blend of the invention can be mixed with a coreactant polyfunctional isocyanate, optionally with catalyst, solvent, or the like, as described above, wherein the resulting pre-polymer is then applied to the fertilizer particles while still in fluid condition. Or, the pre-polymer composition can be formed in situ on the fertilizer particles by separately applying the B-side resin blend and the A-side isocyanate, either concurrently, or sequentially, such that the pre-polymer forms in place, then sets up to provide the polymer coating on the fertilizer particles.

A coated fertilizer of the invention can further comprise a herbicide, an insecticide, or a fungicide, or any combination thereof, such as in the polyurethane coating or in the particle itself. A coated fertilizer particle, can also comprise a micronutrient, e.g. in the polyurethane coating, for controlled release along with the nitrogen of the urea or other N-containing fertilizer, or other element such as P or K, incorporated into the particulate fertilizer.

A particulate fertilizer prepared using in a pre-polymer composition a polyol wherein a third component thereof comprises a polyfunctional aromatic acid, or an anhydride thereof, or an ester thereof, or a mixture thereof, added in the preparation of the polyol composition, can exhibit unexpectedly favorable controlled release properties. As is shown in FIG. 1, and is described in greater detail in the Examples, below, a polyol composition comprising an aromatic functionality comprising the polyfunctional aromatic acid, ester thereof, or anhydride thereof, or mixture thereof, when incorporated into a PU polymer coating for particulate urea fertilizer, exhibits a slower release profile of the fertilizer under field conditions than does a comparable composition having a lesser content of aromatic functionality. In FIG. 1, Recipes 1-5 are prepared according to methods described herein to provide samples having the indicated content of aromatic components, aliphatic components, and hydrophobic components. In FIG. 1, the relative content of each class of component, i.e., aromatic, aliphatic, and hydrophobic, is indicated, and data are shown for 1-day and 3-day fertilizer release results expressed as a relative release profile ranging from 0 to 20, for a 3-4% coating. FIG. 1 indicates a high degree of correlation between the content of aromatic materials in the composition and the delay of release of the fertilizer content. As can be seen, in Recipes 1 and 2, at 70% proportion of aromatic constituents, the relative release profiles are identical despite the altered aliphatic and hydrophobic proportions; however, when aromatic content is decreased and aliphatic content increased, in Recipe 3, relative release profile rates increase, and increase of the hydrophobic proportion in Recipes 4 and 5 results in a yet higher relative release profile.

Accordingly, the invention can provide a method of preparing a coated fertilizer, comprising applying a pre-polymer composition of the invention to a particulate fertilizer material, such as prilled urea or granular urea, wherein a relative release profile is adjustable by modification of relative proportions of aromatic, aliphatic, and hydrophobic components of polyol compositions prepared according to methods disclosed and claimed herein.

The polyol composition used in formation of the polyurethane coating for the particulate fertilizer can be adjusted to provide solutions to various problems involved in production of coated fertilizer particles. Table 3, below, indicates some of the adjustments that can be made when an indication of the stated problem is observed.

TABLE 3

Indications for Adjustment of Polyol Component in PU Polymer Coatings

| Problem | Solution |
| --- | --- |
| Releases too quickly. | Increase coating thickness. Reduce coating permeability per unit thickness. Decrease solubility of the fertilizer (fertilizer to be coated) |
| Releases too slowly | Decrease coating thickness. Increase coating permeability per unit thickness. Increase solubility of the substrate (fertilizer to be coated) |
| Release profile not balanced for target application | Modify aliphatic polyester polyol backbone by optimizing type of glycol use and modifier content. Modifier can include aromatic groups, hydrophobic groups (such as oil), etc |
| Processing issues due to stickiness | Modify pre-polymer composition used in the PU coating by coblending other polyether and/or oils Modify PU coating formulation by adjusting index and/or catalyses Change processing conditions, ex preheat raw materials (to a point) to even out chemical distribution Lower polyol viscosity Modify aliphatic polyester polyol backbone by optimizing type of glycol use and modifier content. Modifier can include aromatic groups, hydrophobic groups (such as oil), etc |
| Processing and handling issues due to coating instability | Modify aliphatic polyester polyol backbone by optimizing type of glycol use and modifier content. Modifier can include aromatic groups, hydrophobic groups (such as oil), etc Increase overall functionality of the polyol by using functionalized glycol. |

The invention can also provide a fiber-reinforced composite material comprising a polyurethane polymer of the invention, or a polyisocyanurate polymer of the invention and a fiber substance. The fiber substance can be cellulosic, such as wood fibers. The invention can also provide a method of preparing a fiber-reinforced composite material, comprising contacting the fiber substance and the pre-polymer composition of the invention, then maintaining the pre-polymer composition in contact with the fiber substance under conditions suitable for the pre-polymer composition to form the solid PU or PIR polymer material of the invention. An Example is provided below.

EXAMPLES

Analysis of NVR, COP Acid, and Polyester Polyols

As noted elsewhere herein, NVR and COP Acid contain mono- and poly-functional molecules bearing alcohol and carboxylic acid functional groups that can react with each other through well-known condensation reactions to form ester linkages. When two or more such monomeric molecules link by formation of ester linkages, the resulting larger molecule is called an ester oligomer. When at least one of the monomeric molecules is polyfunctional, it is possible to form ester oligomers by linking 3 or more monomeric molecules by ester linkages. Ester oligomers, particularly higher molecular weight oligomers, are not amenable to analysis by gas chromatography (GC) because they are not sufficiently volatile or stable. Consequently, GC analysis of NVR "as is" may give an incomplete picture of composition. For example, some of the adipic acid contained in NVR is present as free adipic acid, but some is also present bound in ester oligomers formed by reaction of adipic acid with hydroxyl compounds present in NVR.

One example of such an ester oligomer would be the ester oligomer formed from adipic acid and 6-hydroxycaproic acid. NVR may be derivatized before analysis by treatment with common derivitization agents such as bis(trifluoromethyl)trifluoroacetamide (BSTFA), but even after such treatment, direct analysis of NVR reveals only the amount of free adipic acid, which represents only a fraction of the total adipic acid contained in free and bound or ester oligomeric states.

It has been found to be useful to analyze NVR by a methanolysis method, wherein NVR is allowed to react with excess methanol in the presence of an esterification catalyst such as sulfuric acid. Transesterification of ester oligomers with excess methanol forms monomeric methyl esters that are easily analyzed by GC. The advantage of this analysis method is that it provides an analysis of the contained monomeric species whether they are present as monomers or ester oligomers.

The methanolysis analysis is done by refluxing ~1 g sample and 0.125 g suberic acid internal standard with 10 g of 10% sulfuric acid in methanol. The resulting mixture is diluted with 50 mL deionized water and extracted with three 20-mL portions of methylene chloride. The methylene chloride extracts are analyzed by gas chromatography on an HP-FFAP column using a method that was calibrated using authentic materials of known composition. Table 4, below, summarizes analytical results from several different samples of NVR and COP Acid obtained using the methanolysis method. The table also shows "free adipic acid" as determined by BSTFA derivitization and GC analysis, for comparison with the "total adipic acid" as determined by the methanolysis method.

The exact composition of cyclohexane oxidation byproducts such as water wash, COP Acid, and NVR may vary, but the characteristic difunctional components adipic acid and 6-hydroxycaproic acid are both always present in free and/or bound (i.e. esterified) states. Characteristic monofunctional components include but are not limited to butyric acid, valeric acid, and caproic acid. These monofunctional components can be at least partly removed to form a refined mixture before and/or during formation of the polyester polyol of the present invention is completed.

TABLE 4

Partial composition of NVR and COP Acid

| Component | NVR-A | NVR-B | NVR-C | NVR-D | NVR-E | COP Acid |
|---|---|---|---|---|---|---|
| Water | 22.0 | 27.8 | 23.6 | 19.6 | 23.6 | 38 |
| Total butyric acid | 1.6 | 0.5 | 2.0 | 1.0 | 1.7 | 0.08 |

TABLE 4-continued

Partial composition of NVR and COP Acid

| Component | NVR-A | NVR-B | NVR-C | NVR-D | NVR-E | COP Acid |
|---|---|---|---|---|---|---|
| Total valeric acid | 11.0 | 4.6 | 11.4 | 7.4 | 11.7 | 0.6 |
| Total caproic acid | 4.0 | 2.5 | 3.6 | 3.5 | 4.4 | 0.03 |
| Total succinic acid | 0.5 | 0.6 | 0.4 | 0.4 | 0.4 | 0.7 |
| Total glutaric acid | 2.1 | 1.5 | 1.5 | 1.4 | 1.9 | 2.1 |
| Total adipic acid | 12.4 | 15.3 | 9.3 | 12.1 | 11.3 | 18.9 |
| (Free adipic acid) | 3.1 | 3.9 | 2.7 | 3.0 | 2.9 | Not tested |
| Total hydroxycaproic acid | 14.5 | 22.0 | 16.0 | 19.1 | 12.0 | 20.4 |

Procedures for Applying Coating to Fertilizer

In general, a coating comprises a Part A and a Part B capable of reacting with each other to form a polyurethane polymer. Part B may be a pre-polymer composition comprising at least one polyol and optionally other components as described above. In particular, the other components may include other isocyanate-reactive compounds such as chain extenders or crosslinkers, one or more catalysts, and one or more solvents. Part A comprises at least one isocyanate and optionally one or more solvents. Relative amounts of reactants are calculated to produce polyurethane with the desired isocyanate index, where isocyanate index is calculated as the molar ratio of isocyanate to isocyanate-reactive groups. As described above, isocyanate index may be expressed as a percentage, where 100 indicates a molar ratio of isocyanate to isocyanate-reactive groups of 100%. Isocyanate index may also be expressed as a simple ratio rather than as a percentage and the two expressions are equivalent: for example, an isocyanate index of 1 is equivalent to index of 100% and indicates equal moles of isocyanate and isocyanate-reactive groups while isocyanate index 1.05 is equivalent to 105% and indicates a 5% molar excess of isocyanate over isocyanate-reactive groups.

Coating Procedure A

A Büchi R-210 rotary evaporator is set up with a dry-ice-cooled condenser. A length of ¼" PTFE tubing is attached to the liquid inlet and extends into the upper neck area of the evaporator flask. A water bath is preheated to curing temperature, typically 60-80° C.

A 1 liter, pear-shaped, Büchi rotary-evaporator flask is charged with 150.0 g fertilizer and attached to a Büchi R-210 rotary evaporator. The apparatus is evacuated to 50-60 mm Hg and the fertilizer pre-heated to curing temperature. The evaporator flask is initially rotated at a setting of "2" on the Büchi, corresponding to ~45 rpm.

The Büchi flask is raised from the water bath and a reactant (or mixture or reactants, optionally comprising a solvent) is admitted through the liquid inlet, using vacuum to pull the reactant into the Büchi apparatus through the liquid inlet and PTFE tube onto the fertilizer in the rotating evaporator flask. A small amount of solvent may be used as a "chaser" to rinse reactant adhering to the liquid inlet and PTFE tubing onto the fertilizer.

The rotating Büchi flask is lowered into the water bath and heat/rotation is continued for a time sufficient to coat the reactant(s) onto the fertilizer. Rotation speed is adjusted as necessary to impart a tumbling motion to the flask contents.

Steps 3 and 4 are repeated as necessary to add all reactants necessary to form one single coat.

After all necessary reactants to form one single coat have been admitted, heat and rotation are continued for a time sufficient to cure the coating.

Steps 3 through 6 are repeated as desired to form as many additional coats as desired.

Coating Procedure B

Coating Procedure B is the same as Coating Procedure A except that an alternative version of step 3 is used to minimize solvent usage. In the alternative step 3, the rotary evaporator inlet is not used. Instead, the Büchi flask is removed from the rotary evaporator and reactants are added directly to the Büchi flask. No solvent "chaser" is necessary or used. The flask is shaken by hand for ~30 seconds to disperse the liquid reactants onto the urea. The flask is then attached to the rotary evaporator and the procedure completed as in Coating Procedure A above.

Coating Weight Measurement

The following procedure was used to determine the weight and weight percentage of polymer coating applied to a urea fertilizer.

Approximately 5 g of coated urea fertilizer is weighed into a mortar and a pestle is used to pulverize the coated sample, to disrupt the coating The pulverized sample is transferred to a 150 mL beaker and stirred with ~50 mL deionized water for 10 minutes to dissolve the water-soluble portion of the sample (i.e. the urea). The coating remains undissolved.

A vacuum filtration apparatus is assembled using a vacuum flask, 70 mm Büchner funnel, and a tared piece of Whatman #42 filter paper. The contents of the beaker are poured through the filter assembly to collect the undissolved coating on the filter paper. The beaker is rinsed with ~50 mL additional deionized water to transfer all of the coating onto the tared filter paper.

The filter paper bearing the coating is dried in a 100° C. oven for 1 hour, cooled and weighed. The paper tare weight is subtracted and the coating weight calculated. The weight percentage coating is calculated based on the initial weight of fertilizer used in step 1.

Fertilizer Controlled-Release Testing

The following laboratory test was used to measure relative release rates of coated urea fertilizers. The test does not measure release rate in actual use, but provides a relative measure of the effectiveness of a coating at slowing dissolution of urea in water. Test duration can be any desired time period that reveals a performance difference between the samples of interest. Too short a test duration may not discriminate well if very little release is observed for all test samples. Too long a test duration may not discriminate well if virtually complete release is observed for all test samples. We have found that test duration of 68 hours discriminates performance of some commercial controlled-release urea fertilizers as well as controlled-release fertilizers made using the current invention.

A 20 mL scintillation vial is charged with 2.0 g coated fertilizer and 8.0 g deionized water.

The scintillation vial is capped securely and attached (using elastic bands) to a rotating horizontal shaft so that it will be turned end-over-end at ~7 rpm. The start time is recorded.

After the desired test duration, ~5 mL of liquid is passed through a 0.45 μm syringe filter and the filtrate is collected in a tared aluminum foil weighing pan. The gross weight is recorded and the net weight of filtrate is calculated.

The aluminum pan containing filtrate is placed in a 100° C. nitrogen-purged oven until all water has evaporated. The dry gross weight is recorded and the weight of dry residue is calculated.

The percent solids in the filtrate is calculated from the weight of dry residue from step 4 and the net weight of filtrate measured in step 3.

The maximum percent solids expected if 100% of the urea contained in the coated fertilizer sample dissolved is calculated by subtracting the coating weight from the coated fertilizer weight in step 1 and dividing by total weight of fertilizer and water (10 g). The percent release is calculated by dividing the result of step 5 by the result of step 6.

Polyol Example 1

A polyol with hydroxyl number 168 is prepared using NVR-D and diethylene glycol as follows.

A 3-liter round-bottom flask is charged with 565 g NVR-D (see Table 4) and 225 g diethylene glycol. The flask is fitted with a distillation takeoff, condenser, and distillate receiver, a vacuum connection, magnetic stirrer, and a dip-tube (sparger) to admit nitrogen below the surface of the liquid. The mixture is heated and sparged with nitrogen while pressure is reduced to ~300 mm Hg. Distillate is collected in the distillate receiver. When no more distillate is seen coming overhead, vacuum is broken with nitrogen and the mixture allowed to cool to <100° C. Collected distillate is removed and found to weigh 153 g. Analysis of the distillate shows that it contains monofunctional components including cyclohexanol, butyric acid, valeric acid, and caproic acid but desirable difunctional species including adipic acid and 6-hydroxycaproic acid are not detected. The nitrogen sparger is removed, 0.15 g titanium tetraisopropoxide added, and the mixture heated under vacuum. Temperature is increased to 196° C. and pressure reduced to 142 mm over ~1 hour. Pressure is reduced further to ~42 mm Hg over the course of an additional 2.6 hours, while temperature is maintained in the range 196-200° C. Heat is removed and the mixture allowed to cool under nitrogen.

The reaction mixture is analyzed for hydroxyl number. Hydroxyl number is found to be 158 mg KOH/g. Diethylene glycol (4.56 g) is added and the reaction mixture heated to 180° C. for 1 hour to re-equilibrate the polyol with the added diethylene glycol. The product polyol has hydroxyl number 168 mg KOH/g, viscosity of 324 cSt at 23° C., and weighs 464 g.

The NVR-D starting material and polyol product are both analyzed using the methanolysis method described above. The weight ratio of valeric acid to adipic acid is found to be 0.61 in the NVR-D feed and only 0.32 in the polyol product, showing that the polyol product contains only 52% of the monofunctional valeric acid, relative to adipic acid, as is present in the NVR-D starting material. As noted above, analysis of the condensate shows that the monofunctional components were at least partly removed with the condensate, explaining the reduced amount found in the polyol product. The weight ratio of adipic acid to 6-hydroxycaproic acid is 0.63 in the NVR-D starting material and 0.66 in the polyol product, showing that the relative amounts of those two desirable difunctional molecules is essentially unchanged by the polyol preparation.

Polyol Example 2

A polyol with hydroxyl number 168 is prepared using NVR-E, terephthalic acid, and diethylene glycol as follows.

A 500-mL round-bottom flask is charged with 113 g NVR-E (See Table 4) and 13.5 g terephthalic acid. The flask is fitted with a distillation takeoff, condenser and distillate receiver, a vacuum connection, magnetic stirrer, and a dip-tube (sparger) to admit nitrogen below the surface of the liquid. The mixture is heated to 154° C. and sparged with nitrogen while pressure is reduced to ~143 mm Hg. Distillate is collected in the distillate receiver. When no more distillate is seen coming overhead, vacuum is broken with nitrogen. The mixture is allowed to cool to 91° C., then 0.02 g titanium tetraisopropoxide is added. The mixture is heated to 159° C. and sparged with nitrogen while pressure is reduced to 148 mm Hg. When no more distillate is seen coming overhead, vacuum is broken with nitrogen. The distillate is removed and found to weigh 32.4 g. Diethylene glycol (70 g) is added and the reaction mixture heated to 156° C. and sparged with nitrogen while pressure is reduced to 283 mm Hg. After 3 hours, 0.02 g additional titanium tetraisopropoxide is added, the nitrogen sparge is removed, and the mixture heated under vacuum. Temperature is maintained in the range 174-208° C. while pressure is reduced to 41 mm Hg. After 7.5 hours at these conditions, 57.9 g distillate has been collected. The reaction mixture weighs 104.8 g and analysis shows acid number to be 0.21 mg KOH/g and hydroxyl number to be 131 mg KOH/g. Diethylene glycol (4.23 g) is added and the reaction mixture heated to 180° C. for 1 hour to equilibrate. Heat is removed and the mixture allowed to cool under nitrogen. Final product weight is 109.1 g, acid number is 0.80 mg KOH/g, hydroxyl number is 168 mg KOH/g, and viscosity is 947 cSt at 23° C.

The NVR-E starting material and polyol product are both analyzed using the methanolysis method described above. The weight ratio of valeric acid to adipic acid is found to be 1.04 in the NVR-E feed and only 0.53 in the polyol product, showing that the polyol product contains only 51% of the monofunctional valeric acid, relative to adipic acid, as is present in the NVR-E starting material.

Polyol Example 3

A polyol with hydroxyl number 168 is prepared using NVR-D and neopentyl glycol as follows.

A 500-mL round-bottom flask is charged with 113 g NVR-D (see Table 4) and 68.3 g neopentyl glycol. The flask is fitted with a distillation takeoff, condenser, and distillate receiver, a vacuum connection, magnetic stirrer, and a dip-tube (sparger) to admit nitrogen below the surface of the liquid. The mixture is heated to 151° C. and sparged with nitrogen while pressure is reduced to 298 mm Hg. Distillate is collected in the distillate receiver. When no more distillate is seen coming overhead, vacuum is broken with nitrogen and the mixture allowed to cool to <100° C. The weight of distillate collected is 32.9 g. The nitrogen sparger is removed, 0.03 g titanium tetraisopropoxide added, and the mixture heated and maintained in the range 173-202° C. while pressure is reduced to 40 mm Hg. Heat is removed and the mixture allowed to cool under nitrogen.

The reaction mixture is analyzed for acid number and hydroxyl number. Acid number is found to be 0.41 mg KOH/g. Hydroxyl number is found to be 142 mg KOH/g. Neopentyl glycol (2.50 g) is added and the reaction mixture heated to 180° C. for 1 hour to re-equilibrate the polyol with the added neopentyl glycol. The product polyol has acid number 0.68 mg KOH/g, hydroxyl number 167 mg KOH/g, viscosity of 667 cSt at 23° C., and weighs 89.6 g.

The NVR-D starting material and polyol product are both analyzed using the methanolysis method described above. The weight ratio of valeric acid to adipic acid is found to be 0.61 in the NVR-D feed and only 0.33 in the polyol product, showing that the polyol product contains only 54% of the monofunctional valeric acid, relative to adipic acid, as is present in the NVR-D starting material.

Polyol Example 4

A polyol with hydroxyl number 169 is prepared using NVR-D, terephthalic acid, and diethylene glycol as follows.

A 2 L round-bottom flask is charged with 508.5 g NVR-D (see Table 4) and 60.75 g terephthalic acid. The flask is fitted with a distillation takeoff, condenser and distillate receiver, a vacuum connection, magnetic stirrer, a dip-tube (sparger) to admit nitrogen below the surface of the liquid. The mixture is heated and sparged with nitrogen while pressure is reduced to ~150 mm Hg. Water and low boiling components of NVR distill overhead and are collected in the distillate receiver. When no more distillate is seen coming overhead, vacuum is broken with nitrogen, the mixture is allowed to cool to 118° C., and 0.1 g titanium tetraisopropoxide is added. The reaction mixture is sparged with nitrogen and heated to 160° C. while pressure is reduced to 300 mm Hg. When no more distillate is seen coming over, the vacuum is broken with nitrogen and the mixture is allowed to cool to 69° C. The accumulated distillate is drained from the distillate receiver and found to weigh 143.1 g. Analysis of the distillate shows that it contains monofunctional components including cyclohexanol, butyric acid, valeric acid, and caproic acid but desirable difunctional species including adipic acid and 6-hydroxycaproic acid are not detected. Diethylene glycol (315 g) is added to the reaction mixture. The reaction mixture is sparged with nitrogen and heated to 160° C. while pressure is reduced to 300 mm Hg. After 3 hours, the nitrogen sparge is removed and 0.1 g titanium tetraisopropoxide added. The reaction mixture is heated to 200° C. while pressure is reduced to 150 mm Hg. After 1 hour, pressure is reduced to 40 mm Hg and held for 4.5 hours. Heat is removed and the mixture allowed to cool under nitrogen.

The reaction mixture is analyzed for hydroxyl number. Hydroxyl number is found to be 148 mg KOH/g. Diethylene glycol (10.6 g) is added and the reaction mixture heated to 180° C. for 1 hour to re-equilibrate the polyol with the added diethylene glycol. The product polyol weighs 515 g and has acid number 0.43 mg KOH/g, hydroxyl number 169 mg KOH/g, and viscosity of 773 cSt at 23° C.

The NVR-D starting material and polyol product are both analyzed using the methanolysis method described above. The weight ratio of valeric acid to adipic acid is found to be 0.61 in the NVR-D feed and only 0.31 in the polyol product, showing that the polyol product contains only 51% of the monofunctional valeric acid, relative to adipic acid, as is present in the NVR-D starting material. As noted above, analysis of the condensate shows that the monofunctional components were at least partly removed with the condensate, explaining the reduced amount found in the polyol product.

Polyol Example 5

A polyol with hydroxyl number 168 is prepared using COP Acid and diethylene glycol as follows:

A 500 mL round-bottom flask is charged with 150 g COP Acid (see Table 1). The flask is fitted with a short-path distillation head with condenser, a vacuum connection, a magnetic stirrer, and a nitrogen inlet tube to admit nitrogen below the surface of the liquid. Pressure is reduced to 300 mm Hg and the mixture is heated to 150° C. while sparging with a slow flow of nitrogen. After ~3 hours, 0.03 g titanium tetraisopropoxide is added, the nitrogen inlet tube is removed, pressure is reduced to 40 mm Hg, and the mixture is heated to 200° C. and held for an additional ~3 hours. The mixture is cooled and 45.0 g diethylene glycol is added. Pressure is reduced to 40 mm and the mixture heated to 200° C. for 3.5 hours. The mixture is cooled and acid number found to be 9.3 mg KOH/g. An additional 0.02 g titanium tetraisopropoxide is added, pressure is reduced to 40 mm Hg, and the mixture is heated to 200° C. for an additional 2 hours. Acid number is measured and found to be 0.63 mg KOH/g. Hydroxyl number is measured and found to be 145 mg KOH/g. An additional 2.89 g diethylene glycol is added and the mixture heated to 180° C. at atmospheric pressure and held for 1 hour. The product is found to weigh 119 g. Acid number is found to be 1.01 mg KOH/g, hydroxyl number is found to be 168 mg KOH/g, water content is found to be 0.06 weight %, and viscosity is found to be 542 cSt at 21° C.

The COP Acid starting material and the polyol product are both analyzed using the methanolysis method described above. The weight ratio of valeric acid to adipic acid is found to be 0.0372 in the COP Acid feed and only 0.015 in the polyol product, showing that the polyol product contains only 40% of the monofunctional valeric acid, relative to adipic acid, as is present in the COP Acid starting material. The weight ratio of adipic acid to 6-hydroxycaproic acid is 0.96 in both starting material and product, showing that the relative amounts of those two desirable difunctional molecules is unchanged by the polyol preparation.

Polyol Example 6

A polyol with hydroxyl number 188 is prepared using NVR-D, glycerine, and diethylene glycol as follows.

A 500 mL round-bottom flask is charged with 113 g NVR-D (see Table 4). The flask is fitted with a distillation takeoff, condenser, and distillate receiver, a vacuum connection, magnetic stirrer, and a dip-tube (sparger) to admit nitrogen below the surface of the liquid. The mixture is sparged with nitrogen while pressure is reduced to ~300 mm Hg and the contents heated to 150° C. Distillate is collected in the distillate receiver. After ~4.5 hours, no more distillate is seen coming overhead, vacuum is broken with nitrogen and the mixture allowed to cool. The collected distillate is removed and found to weigh 30.2 g. The nitrogen sparger is removed, 0.3 g titanium tetraisopropoxide, 10.0 g glycerine, and 28 g diethylene glycol are added, and the mixture is heated to 185° C. while pressure is reduced to 40 mm Hg. After 7 hours, the mixture is cooled. Acid number is found to be 1.76 mg KOH/g. About 0.03 g titanium tetraisopropoxide is added and temperature is increased to 200° C. while pressure reduced to 40 mm Hg. After 1 hour, acid number is found to be 0.90 mg KOH/g and hydroxyl number is 223 mg KOH/g. The collected distillate is removed and found to weigh 20.3 g. The reaction mixture is again heated and maintained at 200-212° C. and 40 mm Hg until an additional 6.7 g distillate was collected. Heat is removed and the mixture allowed to cool under nitrogen. The product is found to weigh 88.6 g and has acid number 0.25 mg KOH/g, hydroxyl number 188 mg KOH/g, and viscosity 725 cSt at 23° C.

The NVR-D starting material and polyol product are both analyzed using the methanolysis method described above. The weight ratio of valeric acid to adipic acid is found to be 0.61 in the NVR-D feed and only 0.38 in the polyol product, showing that the polyol product contains only 62% of the monofunctional valeric acid, relative to adipic acid, as is present in the NVR-D starting material.

Polyol Example 7

1500 grams of COP Acid from adipic acid manufacture plant containing 40% water is charged to a 2-liter glass reactor equipped with an agitator, reflux condenser, separation column, overhead receiver, and a thermocouple. The contained physical water is boiled off at temperatures as high as 160° C. After dehydration to less than 1% water, 630 grams of diethylene glycol and esterification catalyst(s) are added. The reaction mixture is taken to a maximum temperature of 235° C. with constant agitation at atmospheric pressure, until theoretical overheads obtained. The acid number of the resulting mixture was lowered to a target specification of <2 mg KOH/gram sample (AN). The analysis of the final product is as follows: OH Value=190 mg KOH/gram sample, AN=1.5 mg KOH/gram sample, viscosity=1390 cps at 25° C. During COP dehydration and esterification steps, monofunctional components are removed and are found to be present in the water byproduct Polyol Example 8

1200 grams of COP Acid from adipic acid manufacture plant containing 40% water is charged. The water from COP acid is removed using the same reaction set-up described in Polyol Example 7. Subsequently, 648 grams diethylene glycol, 200 grams tall oil fatty acids, and catalyst(s) are added and reacted using the same reaction conditions as in Polyol Example 7. The analysis of the final product is as follows: OH Value=1 90 mg KOH/gram sample gram, AN=<2 mg KOH/gram sample, viscosity=250 cps at 25° C.

Polyol Example 9

821 grams of COP Acid from adipic acid manufacture plant containing 40% water is charged in a one-liter reactor and dehydrated using the same reaction set-up described in Polyol Example 7. After dehydration to <1% water, 168 grams diethylene glycol, 32 grams of ethylene glycol, and 16 grams pentaerythritol are added and reacted using the same reaction conditions as in Polyol Example 7. The analysis of the final product is as follows: OH Value=199 mg KOH/gram sample gram, AN=2.8 mg KOH/gram sample, viscosity=1080 cps at 25° C.

Polyol Example 10

A polyol with hydroxyl number 163 is prepared using NVR-E, terephthalic acid, and diethylene glycol as follows.

A 500-mL round-bottom flask is charged with 113 g NVR-E (See Table 4) and 27 g terephthalic acid. The flask is fitted with a distillation takeoff, condenser and distillate receiver, a vacuum connection, magnetic stirrer, and a dip-tube (sparger) to admit nitrogen below the surface of the liquid. The mixture is heated to 154° C. and sparged with nitrogen while pressure is reduced to ~156 mm Hg. Distillate is collected in the distillate receiver. When no more distillate is seen coming overhead, vacuum is broken with nitrogen. The mixture is allowed to cool to 122° C., then 0.02 g titanium tetraisopropoxide is added. The mixture is heated to 154° C. and sparged with nitrogen while pressure is reduced to 153 mm Hg. When no more distillate is seen coming overhead, vacuum is broken with nitrogen. Diethylene glycol (70 g) is added and the reaction mixture heated to 150° C. and sparged with nitrogen while pressure is reduced to 295 mm Hg. After 4 hours, the mixture is allowed to cool. The distillate is removed and found to weigh 33.2 g. An additional 0.02 g additional titanium tetraisopropoxide is added, the nitrogen sparge is removed, and the mixture heated under vacuum. Temperature is maintained in the range 184-202° C. while pressure is reduced to 40 mm Hg. After 6.5 hours, 36 g distillate has been collected. The reaction mixture weighs 138.8 g and analysis shows acid number to be 0.53 mg KOH/g, hydroxyl number to be 163 mg KOH/g, and viscosity to be 1181 cSt at 23° C.

The NVR-E starting material and polyol product are both analyzed using the methanolysis method described above. The weight ratio of valeric acid to adipic acid is found to be 1.04 in the NVR-E feed and only 0.69 in the polyol product, showing that the polyol product contains only 66% of the monofunctional valeric acid, relative to adipic acid, as is present in the NVR-E starting material.

Polyol Example 11 for Rigid Foam Applications

Handmix rigid polyurethane foams were prepared after the aliphatic polyester polyols were prepared as described above. The polyol resin (B-side) for the control is prepared using ingredients of polyurethane foam as used in appliance applications such as select polyethers, catalyst, surfactants, water and 245fa. A separate polyol (B-side) similar to the control was prepared, with portions of the polyether replaced with Polyol Example 9, as shown in Table 5, below. In both runs, the MDI used and the B-sides were precooled to 15 deg C. prior to handmix foaming to enable handling of the blowing agent in the laboratory. The polyurethane foam containing the aliphatic polyester polyols showed equivalent properties to a PUR foam from an all-polyether formulation.

TABLE 5

Polyol Example for Rigid Foam Application

|  | Foam Example | Control Foam |
| --- | --- | --- |
| B-side Components |  |  |
| Polyol Example 9 | 30 | 0 |
| Amine initiated Polyether Polyol (OH = 800) | 35 | 50 |
| Sucrose-glycerine initiated Polyether Polyol (OH = 360) | 35 | 50 |
| Silicone Surfactant | 2 | 2 |
| Catalysts | 2 | 2 |
| Water | 2 | 3 |
| HFC 245-fa | 17 | 20 |
| INDEX | 1.10 | 1.10 |
| Reactivity, seconds |  |  |
| CREAM | 11 | 10 |
| GEL | 35 | 38 |
| T.F. | 45 | 50 |
| E.R. | 45 | 44 |
| Foam Properties |  |  |
| Measured Density, pcf | 2.06 | 2.07 |
| K-factor, initial: | 0.139 | 0.140 |
| Freezer Test, 28D, % vol change | −0.7% | −0.5% |
| Humid Age, 28D, % vol change | 2% | 2% |
| Compressives, Parallel, psi | 36 | 44 |
| Perpendicular, psi | 19 | 21 |

Urea Coating Comparative Example A

Castor-Oil Based Coating on Urea

This example describes use of castor oil to prepare a coated urea using coating procedure A as described above.

A 1-liter pear-shaped Büchi rotary-evaporator flask was charged with 150 g urea prills (Aldrich catalog number 51460, 99.0% purity). A solution of the B-part is prepared from 4.20 g Vertellus DB castor oil (obtained from The Hall-Star Company, hydroxyl number 165 mg KOH/g) and 0.49 g triethanolamine in dry toluene to make a total of 42 g. A solution of the A-part is prepared from 3.30 g polymeric methylene diphenyl diisocyanate (PMCI, Sigma Aldrich product number 372986, 30% NCO) in dry toluene to make a total of 42 g. The amounts of castor oil polyol and isocyanate are calculated to give a combined weight of polyol, triethanolamine, and isocyanate of 8 grams and an isocyanate index of 1.05. Solution A and solution B are each divided into 6 equal portions. One sixth of solution A is combined with one sixth of solution B and the combined solution is immediately admitted to the coating apparatus as described above to make one coat. The coat is allowed to cure for 50 minutes at 60° C. Five additional coats are subsequently added, allowing 50 minutes cure time in between coats, for a total of 6 equal coats. The final coat is allowed to cure for a total of 2.5 hours at 60° C.

The coating weight is measured using the procedure described above and found to be 4.14 percent by weight. The release rate is measured using the procedure described above and found to be 55% in 68 hours.

Urea Coating Comparative Example B

Vigoro® Ultra-Turf® 29-0-4 fertilizer is purchased from Lowe's. The label states that the product contains 29% urea nitrogen, 4.5% of which is slow-release N from coated urea. The exact nature of the coating employed is not disclosed. Visual inspection reveals white uncoated urea as well as green-colored coated urea. The green-colored coated urea particles are physically separated for analysis and release testing.

The coating weight is measured using the procedure described above and found to be 3.1 percent by weight. The release rate is measured using the procedure described above and found to be 72% in 68 hours.

Urea Coating Comparative Example C

Polyon® 43-0-0 controlled-release fertilizer, manufactured by Agrium Advanced Technologies, is purchased from Harrell's. According to product literature, Polyon® 43-0-0 is 100% polymer-coated, controlled-release urea with no uncoated, immediate release urea. The exact nature of the coating employed is not disclosed. Visual inspection shows that all particles are green-colored coated urea.

The coating weight is measured using the procedure described above and found to be 6.0 percent by weight. The release rate is measured using the procedure described above and found to be 3% in 68 hours.

Urea Coating Comparative Example D

Agrium Duration 75 coated urea is tested as above and found to have 4.38 percent by weight coating and release of 12% in 68 hours.

Urea Coating Comparative Example E

Agrium XCU 43-0-0 coated urea is tested as above and found to have 6.36 percent by weight coating and release of 64% in 68 hours.

Urea Coating Comparative Example F

Shaw's Turf Food, SurfCote 36-0-6 fertilizer from Knox Fertilizer is observed to be a mixture of blue-coated urea and brown irregular particles. The blue-coated urea is physically separated from the brown particles, tested as above, and found to have 4.37 percent by weight coating and release of 78% in 68 hours.

Urea Coating Comparative Example G

This example describes use of a predominantly aromatic polyol, Terate® 258 available from INVISTA, to prepare a coated urea using coating procedure A described above.

A 1-liter pear-shaped Büchi rotary-evaporator flask was charged with 150 g urea prills (Aldrich catalog number 51460, 99.0% purity). Solution B is prepared comprising 3.60 g Terate® 258 polyol (INVISTA, hydroxyl number 256 mg KOH/g) and 0.49 g triethanolamine in a 50/50 mixture of dry toluene and dry tetrahydrofuran (THF) to make a total of 42 g. Solution A is prepared comprising 3.91 g polymeric methylene diphenyl diisocyanate (Sigma Aldrich product number 372986, 30% NCO) in dry toluene to make a total of 42 g. The amounts of castor oil polyol and isocyanate are calculated to give a combined weight of polyol, triethanolamine, and isocyanate of 8 grams and an isocyanate index of 105. Solution A and solution B are each divided into 6 equal portions. One sixth of solution A is combined with one sixth of solution B and the combined solution is immediately admitted to the coating apparatus as described above to make one coat. The coat is allowed to cure for 50 minutes at 60° C. Five additional coats are subsequently added, allowing 50 minutes cure time in between coats, for a total of 6 equal coats. The final coat is allowed to cure for a total of 2.5 hours at 60° C.

The coating weight is measured using the procedure described above and found to be 3.80 percent by weight. The release rate is measured using the procedure described above and found to be 16% in 68 hours.

Urea Coating Example 1

This example describes use of NVR-based polyol of the current invention to prepare a coated urea according to procedure A described above.

A 1-liter pear-shaped Büchi rotary-evaporator flask was charged with 150 g urea prills (Aldrich catalog number 51460, 99.0% purity). Solution B is prepared comprising 4.20 g polyol of Polyol Example 1 and 0.49 g triethanolamine in dry toluene to make a total of 42 g. Solution A is prepared comprising 3.34 g polymeric methylene diphenyl diisocyanate (Sigma Aldrich product number 372986, 30% NCO) in dry toluene to make a total of 42 g. The amounts of polyol and isocyanate are calculated to give a combined weight of polyol, triethanolamine, and isocyanate of 8 grams and an isocyanate index of 1.05. Solution A and solution B are each divided into 6 equal portions. One sixth of solution A is combined with one sixth of solution B and the combined solution is immediately admitted to the coating apparatus as described above to make one coat. The coat is allowed to cure for 50 minutes at 60° C. Five additional coats are subsequently added, allowing 50 minutes cure time in between coats, for a total of 6 equal coats. The final coat is allowed to cure for a total of 2.5 hours at 60° C.

The coating weight is measured using the procedure described above and found to be 4.37 percent by weight. The release rate is measured using the procedure described above and found to be 65% in 68 hours.

Urea Coating Example 2

This example describes use of NVR-based polyol of the current invention to prepare a coated urea using procedure B described above.

A 1-liter pear-shaped Büchi rotary-evaporator flask was charged with 150 g granulated urea (Lange-Stegmann Company, St. Louis, Mo.). Solution B is prepared comprising 3.86 g polyol of Polyol Example 1 and 0.49 g triethanolamine in dry toluene to make a total of 12 g. Solution A is prepared comprising 3.15 g polymeric methylene diphenyl diisocyanate (Sigma Aldrich product number 372986, 30% NCO) in dry toluene to make a total of 12 g. The amounts of polyol and isocyanate are calculated to give a combined weight of polyol, triethanolamine, and isocyanate of 7.5 grams and an isocyanate index of 1.05. Solution A and solution B are each divided into 6 equal portions. One sixth of solution A is combined with one sixth of solution B and the combined solution is immediately added to the coating flask as described in procedure B above to make one coat. The coat is allowed to cure for 50-55 minutes at 60° C. Five additional coats are subsequently added, allowing 50-55 minutes cure time in between coats, for a total of 6 equal coats. The final coat is allowed to cure for a total of 2.5 hours at 60° C.

The coating weight is measured using the procedure described above and found to be 4.40 percent by weight. The release rate is measured using the procedure described above and found to be 28% in 68 hours.

Urea Coating Example 3

This example describes use of NVR-based polyol of the current invention to prepare a coated urea using procedure B described above.

A 1-liter pear-shaped Büchi rotary-evaporator flask was charged with 150 g granular urea (Lange-Stegmann Company, St. Louis, Mo.). Solution B is prepared by dissolving 3.86 g polyol of Polyol Example 1 and 0.49 g triethanolamine in dry toluene to make a total of 6 g. Solution A is prepared by dissolving 3.15 g polymeric methylene diphenyl diisocyanate (Sigma Aldrich product number 372986, 30% NCO) in dry toluene to make a total of 6 g. The amounts of polyol and isocyanate are calculated to give a combined weight of polyol, triethanolamine, and isocyanate of 7.5 grams and an isocyanate index of 1.05. Solution A and solution B are each divided into 6 equal portions. One sixth of solution A is combined with one sixth of solution B and the combined solution is immediately added directly to the evaporator flask as described in coating procedure B above to make one coat. The coat is allowed to cure for 30 minutes at 80° C. Five additional coats are subsequently added in the same way, allowing 30 minutes cure time in between coats, for a total of 6 equal coats. The final coat is allowed to cure for a total of 2 hours at 80° C.

The coating weight is measured using the procedure described above and found to be 3.38 percent by weight. The release rate is measured using the procedure described above and found to be 56% in 68 hours.

Urea Coating Example 4

This example describes use of NVR-based polyol of the current invention to prepare a coated urea using procedure B described above.

A 1-liter pear-shaped Büchi rotary-evaporator flask was charged with 139 g of the coated urea from Urea Coating Example 2 above. Solution B is prepared by dissolving 3.86 g polyol of Polyol Example 1 and 0.49 g triethanolamine in dry toluene to make a total of 12 g. Solution A is prepared by dissolving 3.15 g polymeric methylene diphenyl diisocyanate (Sigma Aldrich product number 372986, 30% NCO) in dry toluene to make a total of 12 g. The amounts of polyol and isocyanate are calculated to give a combined weight of polyol, triethanolamine, and isocyanate of 7.5 grams and an isocyanate index of 1.05. Solution A and solution B are each divided into 6 equal portions. One sixth of solution A is combined with one sixth of solution B and the combined solution is immediately added directly to the evaporator flask as described in coating procedure B above to make one coat. The coat is allowed to cure for 50 minutes at 60° C. Five additional coats are subsequently added in the same way, allowing 50 minutes cure time in between coats, for a total of 6 equal coats. The final coat is allowed to cure for a total of 2.5 hours at 60° C. Since the coated urea from Urea Coating Example 2 already had 6 coats, the product of this example has a total of 12 coats.

The coating weight is measured using the procedure described above and found to be 7.24 percent by weight. The release rate is measured using the procedure described above and found to be 5% in 68 hours.

Urea Coating Example 5

This example describes use of NVR-based polyol of the current invention to prepare a coated urea according to procedure A described above.

A 1-liter pear-shaped Büchi rotary-evaporator flask was charged with 150 g urea prills (Aldrich catalog number 51460, 99.0% purity). Solution B is prepared comprising 3.85 g polyol of Polyol Example 6 and 0.49 g triethanolamine in dry toluene to make a total of 42 g. Solution A is prepared comprising 3.63 g polymeric methylene diphenyl diisocyanate (Sigma Aldrich product number 372986, 30% NCO) in dry toluene to make a total of 42 g. The amounts of polyol and isocyanate are calculated to give a combined weight of polyol, triethanolamine, and isocyanate of 8 grams and an isocyanate index of 1.15. Solution A and solution B are each divided into 6 equal portions. One sixth of solution A is combined with one sixth of solution B and the combined solution is immediately admitted to the coating apparatus as described in Coating Procedure A above to make one coat. The coat is allowed to cure for 50 minutes at 60° C. Five additional coats are subsequently added, allowing 50 minutes cure time in between coats, for a total of 6 equal coats. The final coat is allowed to cure for a total of 2.5 hours at 60° C.

The coating weight is measured using the procedure described above and found to be 3.46 percent by weight. The release rate is measured using the procedure described above and found to be 35% in 68 hours.

Urea Coating Example 6

This example describes use of NVR-based polyol of the current invention to prepare a coated urea according to procedure A described above.

A 1-liter pear-shaped Büchi rotary-evaporator flask was charged with 150 g urea prills (Aldrich catalog number 51460, 99.0% purity). Solution B is prepared comprising 5.35 g polyol of Polyol Example 1 and 0.10 g DABCO 8154® catalyst (Air Products) in dry toluene to make a total of 42 g. Solution A is prepared comprising 2.53 g polymeric methylene diphenyl diisocyanate (Sigma Aldrich product number 372986, 30% NCO) in dry toluene to make a total of 42 g. The amounts of polyol (including hydroxyl content of the DABCO 8154® catalyst) and isocyanate are calculated to give a combined weight of polyol, DABCO®, and isocyanate of 8 grams and an isocyanate index of 1.05. Solution A and solution B are each divided into 6 equal portions. One sixth of solution A is combined with one sixth of solution B and the combined solution is immediately admitted to the coating apparatus as described above to make one coat. The coat is allowed to cure for 45 minutes at 60° C. and 55 mm Hg. Five additional coats are subsequently added in a similar manner, allowing 45-55 minutes cure time in between coats, for a total of 6 equal coats. The final coat is allowed to cure for a total of 2.5 hours at 60° C.

The coating weight is measured using the procedure described above and found to be 4.45 percent by weight. The release rate is measured using the procedure described above and found to be 86% in 68 hours.

Urea Coating Example 7

This example describes use of NVR-based polyol of the current invention to prepare a coated urea using procedure B described above and toluene solvent.

A 1-liter pear-shaped Büchi rotary-evaporator flask was charged with 150 g granular urea (Lange-Stegmann Company, St. Louis, Mo.). Solution B is prepared by dissolving 3.92 g polyol of Polyol Example 7 and 0.49 g triethanolamine in dry toluene to make a total of 9 g. Solution A is prepared by dissolving 3.09 g polymeric methylene diphenyl diisocyanate (Sigma Aldrich product number 372986, 30% NCO) in dry toluene to make a total of 9 g. The amounts of polyol and isocyanate are calculated to give a combined weight of polyol, triethanolamine, and isocyanate of 7.5 grams and an isocyanate index of 1.05. Solution A and solution B are each divided into 6 equal portions. One sixth of solution A is combined with one sixth of solution B and the combined solution is immediately added directly to the evaporator flask as described in coating procedure B above to make one coat. The coat is allowed to cure for 50 minutes at 60° C.

Five additional coats are subsequently added in the same way, allowing 50 minutes cure time in between coats, for a total of 6 equal coats. The final coat is allowed to cure for a total of 2.5 hours at 60° C.

The coating weight is measured using the procedure described above and found to be 3.40 percent by weight. The release rate is measured using the procedure described above and found to be 11% in 68 hours.

Urea Coating Example 8

This example describes use of NVR-based polyol of the current invention to prepare a coated urea using procedure B described above and t-butyl acetate solvent.

A 1-liter pear-shaped Büchi rotary-evaporator flask was charged with 150 g granular urea (Lange-Stegmann Company, St. Louis, Mo.). Solution B is prepared by dissolving 3.86 g polyol of Polyol Example 1 and 0.49 g triethanolamine in dry t-butyl acetate to make a total of 9 g. Solution A is prepared by dissolving 3.15 g polymeric methylene diphenyl diisocyanate (Sigma Aldrich product number 372986, 30% NCO) in dry t-butyl acetate to make a total of 9 g. The amounts of polyol and isocyanate are calculated to give a combined weight of polyol, triethanolamine, and isocyanate of 7.5 grams and an isocyanate index of 1.05. Solution A and solution B are each divided into 6 equal portions. One sixth of solution A is combined with one sixth of solution B and the combined solution is immediately added directly to the evaporator flask as described in coating procedure B above to make one coat. The coat is allowed to cure for 50 minutes at 60° C. Five additional coats are subsequently added in the same way, allowing 50 minutes cure time in between coats, for a total of 6 equal coats. The final coat is allowed to cure for a total of 2.5 hours at 60° C.

The coating weight is measured using the procedure described above and found to be 3.52 percent by weight. The release rate is measured using the procedure described above and found to be 22% in 68 hours.

Urea Coating Example 9

This example describes use of NVR-based polyol of the current invention to prepare a coated urea using procedure B described above and toluene solvent.

A 1-liter pear-shaped Büchi rotary-evaporator flask was charged with 150 g granular urea (Lange-Stegmann Company, St. Louis, Mo.). Solution B is prepared by dissolving 3.86 g polyol of Polyol Example 6 and 0.49 g triethanolamine in dry toluene to make a total of 9 g. Solution A is prepared by dissolving 3.26 g polymeric methylene diphenyl diisocyanate (Sigma Aldrich product number 372986, 30% NCO) in dry toluene to make a total of 9 g. The amounts of polyol and isocyanate are calculated to give a combined weight of polyol, triethanolamine, and isocyanate of 7.5 grams and an isocyanate index of 1.03. Solution A and solution B are each divided into 6 equal portions. One sixth of solution A is combined with one sixth of solution B and the combined solution is immediately added directly to the evaporator flask as described in coating procedure B above to make one coat. The coat is allowed to cure for 50 minutes at 60° C.

Five additional coats are subsequently added in the same way, allowing 50 minutes cure time in between coats, for a total of 6 equal coats. The final coat is allowed to cure for a total of 2.5 hours at 60° C.

The coating weight is measured using the procedure described above and found to be 3.25 percent by weight. The release rate is measured using the procedure described above and found to be 27% in 68 hours.

Urea Coating Example 10

This example describes use of NVR-based polyol of the current invention to prepare a coated urea using procedure B described above and acetone solvent.

A 1-liter pear-shaped Büchi rotary-evaporator flask was charged with 150 g granular urea (Lange-Stegmann Company, St. Louis, Mo.). Solution B is prepared by dissolving 3.86 g polyol of Polyol Example 1 and 0.49 g triethanolamine in dry acetone to make a total of 9 g. Solution A is prepared by dissolving 3.15 g polymeric methylene diphenyl diisocyanate (Sigma Aldrich product number 372986, 30% NCO) in dry acetone to make a total of 9 g. The amounts of polyol and isocyanate are calculated to give a combined weight of polyol, triethanolamine, and isocyanate of 7.5 grams and an isocyanate index of 1.05. Solution A and solution B are each divided into 6 equal portions. One sixth of solution A is combined with one sixth of solution B and the combined solution is immediately added directly to the evaporator flask as described in coating procedure B above to make one coat. The coat is allowed to cure for 50 minutes at 60° C.

Five additional coats are subsequently added in the same way, allowing 50 minutes cure time in between coats, for a total of 6 equal coats. The final coat is allowed to cure for a total of 2.5 hours at 60° C.

The coating weight is measured using the procedure described above and found to be 4.25 percent by weight. The release rate is measured using the procedure described above and found to be 48% in 68 hours.

Urea Coating Example 11

This example describes use of NVR-based polyol of the current invention to prepare a coated urea according to procedure A described above.

A 1-liter pear-shaped Büchi rotary-evaporator flask was charged with 150 g urea prills (Aldrich catalog number 51460, 99.0% purity). Solution B is prepared comprising 4.20 g polyol of Polyol Example 2 and 0.49 g triethanolamine in dry toluene to make a total of 42 g. Solution A is prepared comprising 3.33 g polymeric methylene diphenyl diisocyanate (Sigma Aldrich product number 372986, 30% NCO) in dry toluene to make a total of 42 g. The amounts of polyol and isocyanate are calculated to give a combined weight of polyol, triethanolamine, and isocyanate of 8 grams and an isocyanate index of 105. Solution A and solution B are each divided into 6 equal portions. One sixth of solution A is combined with one sixth of solution B and the combined solution is immediately admitted to the coating apparatus as described above to make one coat. The coat is allowed to cure for 50 minutes at 60° C. Five additional coats are subsequently added, allowing 50 minutes cure time in between coats, for a total of 6 equal coats.

The final coat is allowed to cure for a total of 2.5 hours at 60° C.

The coating weight is measured using the procedure described above and found to be 4.50 percent by weight. The release rate is measured using the procedure described above and found to be 43% in 68 hours.

Urea Coating Example 12

This example describes use of NVR-based polyol of the current invention to prepare a coated urea using procedure B described above.

A 1-liter pear-shaped Büchi rotary-evaporator flask was charged with 150 g granular urea (Lange-Stegmann Company, St. Louis, Mo.). Solution B is prepared by dissolving 3.86 g polyol of Polyol Example 1 and 0.49 g triethanolamine in dry DBE®-LVP ester to make a total of 6 g. Solution A is prepared by dissolving 3.15 g polymeric methylene diphenyl diisocyanate (Sigma Aldrich product number 372986, 30% NCO) in dry DBE®-LVP ester to make a total of 6 g. The amounts of polyol and isocyanate are calculated to give a combined weight of polyol, triethanolamine, and isocyanate of 7.5 grams and an isocyanate index of 105. Solution A and solution B are each divided into 6 equal portions. One sixth of solution A is combined with one sixth of solution B and the combined solution is immediately added directly to the evaporator flask as described in coating procedure B above to make one coat. The coat is allowed to cure for 30 minutes at 80° C. Five additional coats are subsequently added in the same way, allowing 30 minutes cure time in between coats, for a total of 6 equal coats. The final coat is allowed to cure for a total of 2 hours at 80° C.

The coating weight is measured using the procedure described above and found to be 3.29 percent by weight. The release rate is measured using the procedure described above and found to be 100% in 68 hours.

Urea Coating Example 13

This example describes use of NVR-based polyol of the current invention to prepare a coated urea using procedure B described above.

A 1-liter pear-shaped Büchi rotary-evaporator flask was charged with 150 g granular urea (Lange-Stegmann Company, St. Louis, Mo.). Solution B is prepared by dissolving 3.86 g polyol of Polyol Example 1 and 0.49 g triethanolamine in dry propylene carbonate to make a total of 6 g. Solution A is prepared by dissolving 3.15 g polymeric methylene diphenyl diisocyanate (Sigma Aldrich product number 372986, 30% NCO) in dry propylene carbonate to make a total of 6 g. The amounts of polyol and isocyanate are calculated to give a combined weight of polyol, triethanolamine, and isocyanate of 7.5 grams and an isocyanate index of 105. Solution A and solution B are each divided into 6 equal portions. One sixth of solution A is combined with one sixth of solution B and the combined solution is immediately added directly to the evaporator flask as described in coating procedure B above to make one coat. The coat is allowed to cure for 50 minutes at 60° C. Five additional coats are subsequently added in the same way, allowing 30 minutes cure time in between coats, for a total of 6 equal coats. The final coat is allowed to cure for a total of 2.5 hours at 60° C.

The coating weight is measured using the procedure described above and found to be 3.43 percent by weight. The release rate is measured using the procedure described above and found to be 100% in 68 hours.

Urea Coating Example 14

This example describes use of NVR-based polyol of the current invention to prepare a coated urea according to procedure A described above.

A 1-liter pear-shaped Büchi rotary-evaporator flask was charged with 150 g urea prills (Aldrich catalog number 51460, 99.0% purity). Solution B is prepared comprising 4.00 g polyol of Polyol Example 1, 0.10 g DABCO 8154® catalyst (Air Products) and 0.49 g triethanolamine in dry toluene to make a total of 42 g. Solution A is prepared comprising 3.40 g polymeric methylene diphenyl diisocyanate (Sigma Aldrich product number 372986, 30% NCO) in dry toluene to make a total of 42 g. The amounts of polyol and isocyanate are calculated to give a combined weight of polyol, triethanolamine, and isocyanate of 8 grams and an isocyanate index of 105. Solution A and solution B are each divided into 6 equal portions. One sixth of solution A is combined with one sixth of solution B and the combined solution is immediately admitted to the coating apparatus as described above to make one coat. The coat is allowed to cure for 50 minutes at 60° C. Five additional coats are subsequently added, allowing 50 minutes cure time in between coats, for a total of 6 equal coats. The final coat is allowed to cure for a total of 2.5 hours at 60° C.

The coating weight is measured using the procedure described above and found to be 3.90 percent by weight. The release rate is measured using the procedure described above and found to be 71% in 68 hours.

Urea Coating Example 15

This example describes use of NVR-based polyol of the current invention to prepare a coated urea according to procedure A described above.

A 1-liter pear-shaped Büchi rotary-evaporator flask was charged with 150 g urea prills (Aldrich catalog number 51460, 99.0% purity). Solution B is prepared comprising 3.95 g polyol of Polyol Example 1 and 0.49 g triethanolamine in dry toluene to make a total of 42 g. Solution A is prepared comprising 3.58 g polymeric methylene diphenyl diisocyanate (Sigma Aldrich product number 372986, 30% NCO) in dry toluene to make a total of 42 g. The amounts of polyol and isocyanate are calculated to give a combined weight of polyol, triethanolamine, and isocyanate of 8 grams and an isocyanate index of 105. Solution A and solution B are each divided into 6 equal portions. One sixth of solution A is combined with one sixth of solution B and the combined solution is immediately admitted to the coating apparatus as described above to make one coat. The coat is allowed to cure for 50 minutes at 60° C. Five additional coats are subsequently added, allowing 50 minutes cure time in between coats, for a total of 6 equal coats. After the 6$^{th}$ coat had cured, 0.1 g Exxal 13 isotridecyl alcohol (ExxonMobil Chemical) in toluene was added and allowed to cure for 2 hours at 60° C.

The coating weight is measured using the procedure described above and found to be 4.18 percent by weight. The release rate is measured using the procedure described above and found to be 45% in 68 hours.

TABLE 6

Summary of Urea Coating Results

| Coating example | Polyol example | Wt % coating | Release % |
|---|---|---|---|
| Comparative Example C | — | 6.04 | 3% |
| Urea Coating Example 4 | 1 | 7.24 | 5% |
| Urea Coating Example 7 | 7 | 3.40 | 11% |
| Comparative Example D | — | 4.38 | 12% |
| Comparative Example G | — | 3.80 | 16% |
| Urea Coating Example 8 | 1 | 3.52 | 22% |
| Urea Coating Example 9 | 6 | 3.25 | 27% |
| Urea Coating Example 2 | 1 | 4.40 | 28% |
| Urea Coating Example 5 | 6 | 3.46 | 35% |
| Urea Coating Example 11 | 2 | 4.50 | 43% |
| Urea Coating Example 15 | 1 | 4.18 | 45% |
| Urea Coating Example 10 | 1 | 4.25 | 48% |
| Comparative Example A | — | 4.14 | 55% |
| Urea Coating Example 3 | 1 | 3.38 | 56% |
| Comparative Example E | — | 6.36 | 64% |
| Urea Coating Example 1 | 1 | 4.37 | 65% |
| Comparative Example B | — | 3.10 | 70% |
| Urea Coating Example 14 | 1 | 3.90 | 71% |
| Comparative Example F | — | 4.31 | 78% |
| Urea Coating Example 6 | 1 | 4.45 | 86% |
| Urea Coating Example 12 | 1 | 3.29 | 100% |
| Urea Coating Example 13 | 1 | 3.43 | 100% |

Table 6, above, summarizes coating weight and release test results for Urea Coating Examples of the present invention and for Comparative Examples. It is easily seen from the Table that Comparative Examples exhibit release rates over a very wide range of 3% to as high as 78% and that Urea Coating Examples of the present invention span a similar range of release rates depending on composition of the polyol, composition of the pre-polymer composition, thickness of the coating, and other details of the coating process. The current invention provides polyols, pre-polymer compositions, and coatings that can be tailored to achieve a wide range of release rates.

Spray Foam Extrudate Fertilizer

A polyurethane encapsulated, slow release fertilizer with a coating based upon an isocyanate component and an isocyanate-reactive component comprising a polyol. The process for producing such particles comprises applying an isocyanate-reactive component comprising a polyol onto fertilizer particles to form coated fertilizer particles, applying an isocyanate component onto said coated fertilizer particles; and forming the polyurethane encapsulated fertilizer particles.

A spray foam formulation is made by preparing the following "B" side blend: 76.40% by weight of a polyol with hydroxyl number 168, prepared according to Example 1 from NVR-D and diethylene glycol; 5.00% by wt. of Saytex®

RB-79 obtained from Albermarle® Corporation; 1.00% by wt. of DABCO DC 193®; 3.00% by wt. Polycat® 30 obtained from Air Products; 2.00% by wt. of Pluracol® 220 from BASF Corporation; 8.00% by wt. of Enovate™ 3000 (HFC-245fa) from Honeywell; 3.00% by wt. of Toyocat® TRX from Tosoh Specialty Chemicals USA, Inc. and 1.60% by wt. of water. This "B" side blend is sprayed with an "A" side polyisocyanate obtained from Huntsman Corp. under the trade name Rubinate® M at a volume ratio of 1:1 through a high pressure spray foam machine.

The resulting foam from the spray machine is directed onto a mass of urea prills (Aldrich catalog number 51460, 99.0% purity) such that the urea prills comprise about 10 weight percent of the total mass of the resulting foam. Without the urea content the foam would have a density of 1.80 pounds per cubic foot with a compressive strength exceeding 21 psig in the parallel direction to rise and a closed cell content of greater than 94%. The foam when sprayed at room temp (72° F./>20% RH) shows good adhesion on the urea substrate.

Alternatively, the "A" side and "B" side blend may be co-linearly guided with an air conveyed mass of urea prills using any suitable extrusion means known in the art to provide an extrudate comprising a urea distributed throughout the foam.

The extrudate may be further processed in short sections for use as a urea slow release fertilizer with a coating based upon an isocyanate component and an isocyanate-reactive component comprising a polyol.

Aliphatic Polyester Polyols for Use in Wood-Binding Applications

The use of polyurethane binders in the preparation of synthetic board from cellulosic and/or lignocellulosic material has been described in the literature including U.S. Pat. Nos. 4,609,513, 4,752,637, 4,833,182, 4,898,776, incorporated herein by reference in their entireties.

Aliphatic polyester polyols from the byproducts of cyclohexane oxidation are used to prepare polyurethane based binder for use in the preparation of a synthetic board from cellulosic and/or lignocellulosic materials.

A polyol can be prepared from the following ingredients in the indicated proportions, having OH values ranging from 100 to 400:

Preparation of Aliphatic Polyester Polyol for Use in Wood-binding Applications

| Ingredients* | Quantity |
|---|---|
| Byproducts from cyclohexane oxidation process as described above | 60-70% |
| Diethylene glycol | 30-40% |
| Catalyst | |

Procedure:

840 grams of predried byproduct as described herein from the cyclohexane oxidation process and 420 grams of diethylene glycol are charged to a 2-liter, 3-necked, round bottom flask equipped with a stirrer, thermometer and a vigreaux column. A titanate based catalyst is added at 150° C. and the ingredients are heated to 235° C. until all 99.5% of the theoretical water is removed, and the following properties are achieved:

Acid Number<2 mg KOH/gram sample.

Hydroxyl values between 150-180 mg KOH/gram sample

Viscosity<1000 cps at 25 deg C.

Polyurethane Binder Composition

The polyurethane binder consists of the polyol blend reacted with polyisocyanate. The polyol blend can consist of the aliphatic polyester polyol listed above, aromatic polyester polyols, other polyethers, polyurethane catalyst, and a surfactant. The polyisocyanate of the binder system is any organic polyisocyanate compound with at least 2 active isocyanate groups per molecule or mixtures of such compounds.

Binder Composition:

| Polyol Blend | 10-50% |
|---|---|
| Aliphatic polyester polyol = | 50-100% |
| Aromatic polyester polyols = | 0-50% |
| Other polyethers = | 0-50% |
| Surfactant = | 0-5% |
| Polyurethane catalyst = | 0-5% |
| Polyisocyanate | 50-90% |

Wood Binding Process Using Polyurethane Binder with Polyester Polyols of the Invention (Example Referenced from U.S. Pat. No. 4,609,513, Incorporated by Reference Herein in its Entirety.)

Wood fibers are treated sequentially with 1% of the polyol blend described above followed by 3% of polyisocyanate such as Rubinate M. The treated furnish is compression molded at about 500 psi pressure and temperature of about 350 deg F. between untreated steel plattens. The operation is repeated 40-50 times and then terminated with the fiberboards still releasing without sticking at the end.

STATEMENTS OF THE INVENTION

1. A method of preparing a polyol composition, the method comprising:
heating a byproduct mixture comprising:
i) a water extract of a cyclohexane oxidation reaction product, optionally concentrated; or,
ii) a non-volatile residue of a cyclohexane oxidation reaction product, optionally concentrated; or a mixture thereof,
and, one or more polyhydroxy compound, and optionally, a catalyst;
optionally under vacuum, or optionally with an inert gas sparge;
to remove monofunctional components and water by distillation.

2. The method of statement 1, further comprising a step of heating the byproduct mixture, optionally under vacuum, or optionally with an inert gas sparge, to remove monofunctional components and water, prior to adding the one or more polyhydroxy compounds, then, after adding the one or more polyhydroxy compounds, continuing to heat the resulting mixture.

3. The method of statements 1 or 2 wherein a remaining content of the monofunctional compounds following the step of heating and removal thereof by distillation is about 10% or less, or is about 5% or less, or is about 2% or less, by weight, of the composition.

4. The method of any one of statements 1-3, wherein the monofunctional components include monocarboxylic acids and monohydric alcohols.

5. The method of any one of statements 1-4, wherein the polyhydroxy compound comprises a diol, a triol, a tetraol, a saccharide, or a sugar alcohol, or any combination thereof.

6. The method of any one of statements 1-4, wherein the polyhydroxy compound is ethylene glycol, diethylene glycol, polyethelene glycol, propylene glycol, dipropylene glycol, polypropylene glycol, butanediol, pentanediol, hexanediol, glycerine, trimethylolpropane, pentaerythritol, or sorbitol, or a combination thereof.

7. The method of any one of statements 1-6, further comprising adding to the byproduct mixture a third component comprising a polyfunctional acid, or an activated ester thereof, or a polyfunctional ester thereof, or an anhydride thereof, or a combination thereof, to the byproduct mixture, then heating and removing monofunctional compounds by distillation.

8. The method of statement 7, wherein the third component comprises a polyfunctional aromatic acid, or an anhydride thereof, or an activated ester thereof, or a polyfunctional ester thereof, or a mixture thereof.

9. The method of statement 8, wherein the third component comprises terephthalic acid, isophthalic acid, orthophthalic acid, trimellitic acid, pyromellitic acid; the activated ester thereof, the polyfunctional ester thereof, or the anhydride thereof; or any combination thereof.

10. The method of statement 7, wherein the third component comprises a polyfunctional aliphatic acid, or an activated ester thereof, or a polyfunctional ester thereof, or an anhydride thereof; or a mixture thereof.

11. The method of statement 10, wherein the third component comprises glycolic acid, citric acid, lactic acid, malic acid, fumaric acid, maleic acid, succinic acid, glutaric acid, or adipic acid; or an activated ester thereof; or a polyfunctional ester thereof; or an anhydride thereof; or a mixture thereof.

12. The method of any one of statements 1-11, further comprising adding to the byproduct mixture a polyfunctional crosslinker or chain extender with two or more reactive hydroxyl or amino functionalities.

13. The method of statement 12, wherein the polyfunctional crosslinker or chain extender is ethylene glycol, diethylene glycol, triethylene glycol, propylene glycol, dipropylene glycol, tripropylene glycol, 1,3-propanediol, 1,3-butanediol, 1,4-butanediol, 1,6-hexanediol, cyclohexane dimethanol, hydroquinone bis(2-hydroxyethyl)ether, neopentyl glycol, glycerol, ethanolamine, diethanolamine, triethanolamine, methyl diethanolamine, phenyl diethanolamine, trimethylolpropane, 1,2,6-hexanetriol, pentaerythritol, N,N,N',N'-tetrakis-(2-hydroxypropyl)ethylenediamine, diethyltoluenediamine, or dimethylthiotoluenediamine; or any mixture thereof.

14. The method of statement 12, wherein the polyfunctional crosslinker or chain extender has three or more reactive hydroxyl or amino functionalities.

15. The method of statement 14, wherein the polyfunctional crosslinker or chain extender is glycerol, triethanolamine, trimethylolpropane, 1,2,6-hexanetriol, pentaerythritol, or N,N,N',N'-tetrakis-(2-hydroxypropyl)ethylenediamine; or any mixture thereof.

16. The method of any one of statements 1-15, comprising adding the catalyst to the byproduct mixture, wherein the catalyst comprises an organometallic compound or a strong acid.

17. The method of statement 16, wherein the organometallic compound comprises an organomercury, organolead, organoferric, organotin, organobismuth, or organozinc compound, or the strong acid comprises toluenesulfonic acid or xylenesulfonic acid.

18. The method of statement 16, wherein the organometallic compound is tetraisopropyl titanate or dibutyl tin dilaurate.

19. The method of any one of statements 1-18, further comprising adding a hydrophobic material to the byproduct mixture, then heating and removing monofunctional components by distillation.

20. The method of statement 19, wherein the hydrophobic material comprises a natural oil, a fatty acid or a fatty acid ester derived therefrom; or a mixture thereof.

21. The method of statement 19, wherein the hydrophobic material comprises a plant oil, a fatty acid or a fatty acid ester derived therefrom; or a mixture thereof.

22. The method of statement 19, wherein the hydrophobic material comprises an animal oil, a fatty acid or a fatty acid ester derived therefrom, and mixtures thereof.

23. The method of statement 19, wherein the hydrophobic material comprises one or more of tallow oil, tall oil fatty acid, soybean oil, coconut oil, castor oil, linseed oil, a nonedible plant-derived oil, or an edible plant-derived oil.

24. The method of statement 19, wherein the hydrophobic material comprises a synthetic oil, a synthetic fatty acid, or a synthetic fatty ester.

25. The method of statement 19, wherein the hydrophobic material is an aminated material, a hydroxylated material, or a combination thereof.

26. The method of any one of statements 1-25 wherein the polyol composition has an OH value of about 100 to 500 mg KOH/gm of sample; or, wherein the composition has an acid number of less than 10 mg KOH/gm of sample, or less than 5 mg KOH/gm of sample, or preferably less than 1 mg KOH/gm of sample; or any combination thereof.

27. The method of any one of statements 1-26, further comprising addition of another polyol, a solvent, a catalyst, a chain extender, a crosslinking agent, a curative, a surfactant, a blowing agent, a filler, a flame retardant, a plasticizer, a light stabilizer, a colorant, a wax, a biocide, a mineral, a micronutrient, an inhibitor, a stabilizer, or an organic or inorganic additive.

28. The method of any one of statements 1-27 wherein the byproduct mixture is a byproduct mixture of an adipic acid manufacturing process, or is a byproduct mixture of a caprolactam manufacturing process, or is a mixture thereof.

29. A polyol composition prepared by the method of any one of statements 1-28.

30. A resin blend comprising the polyol composition of statement 29, and optionally further comprising a catalyst, a chain extender, a crosslinking agent, a curative, a surfactant, a blowing agent, a filler, a flame retardant, a plasticizer, a light stabilizer, a colorant, a wax, a biocide, a mineral, a micronutrient, an inhibitor, a stabilizer, an organic, or an inorganic additive.

31. The resin blend of statement 30, comprising a catalyst suitable for catalyzing formation of a polyurethane or polyisocyanurate polymer when the resin blend containing the catalyst is contacted with a polyfunctional isocyanate.

32. A method of preparing a polyurethane polymer, comprising combining the polyol composition of statement 29 or the resin blend of statement 30, and a polyfunctional isocyanate, under conditions suitable to provide the polyurethane polymer.

33. The method of statement 32 wherein the polyfunctional isocyanate comprises a monomeric MDI, a polymeric MDI, an aliphatic diisocyanate, a cycloaliphatic diisocyanate, an aromatic diisocyanate, a multifunctional aromatic isocyanate, an organic polyisocyanate, a modified polyisocyanate, an isocyanate-based prepolymer, or a mixture thereof.

34. The method of statement 32, wherein the polyfunctional isocyanate comprises three or more isocyanate groups.

35. The method of statement 34, wherein the polyfunctional isocyanate is a polymeric MDI.

36. The method of any one of statements 32-35, further comprising adding a catalyst to the polyol composition and the polyfunctional isocyanate.

37. The method of statement 36, wherein the catalyst comprises an amine or an organometallic compound or a metal carboxylate.

38. The method of statement 37, wherein the amine comprises triethanolamine or diazobicyclooctane, or wherein the metal carboxylate comprises potassium acetate or potassium octoate.

39. The method of any one of statements 32-38, further comprising adding a solvent to the polyol composition and the polyfunctional isocyanate.

40. The method of statement 39, wherein the solvent comprises a hydrocarbon.

41. The method of statement 39, wherein the solvent comprises toluene.

42. A polyurethane polymer prepared by the method of any one of statements 32-41.

43. A method of preparing a polyisocyanurate polymer, comprising mixing the polyol composition of statement 29 or the resin blend of statement 30, and a polyfunctional isocyanate, under conditions suitable to provide the polyisocyanurate polymer.

44. The method of statement 43, wherein the polyfunctional isocyanate is MDI.

45. The method of any one of statements 43-44, further comprising adding a catalyst to the polyol composition and the polyfunctional isocyanate.

46. The method of statement 45, wherein the catalyst comprises an amine, an organometallic compound, or a metal carboxylate.

47. The method of statement 46, wherein the amine comprises triethanolamine or diazobicyclooctane, or the organometallic compound comprises tetraisopropyl titanate or dibutyl tin dilaurate, or wherein the metal carboxylate comprises potassium acetate or potassium octoate.

48. A polyisocyanurate polymer prepared by the method of any one of statements 43-47.

49. A method of preparing a pre-polymer composition for formation of a solid polymer, comprising combining the polyol composition of statement 29 or the resin blend of statement 30, and a coreactant, and optionally, a catalyst, and optionally, a solvent, and optionally, one or more additional ingredient selected from the group consisting of another polyol, a solvent, a catalyst, a chain extender, a crosslinking agent, a curative, a surfactant, a blowing agent, a filler, a flame retardant, a plasticizer, a light stabilizer, a colorant, a wax, a biocide, a mineral, a micronutrient, an inhibitor, a stabilizer, an organic additive, and an inorganic additive.

50. The method of statement 49, wherein the polymer is a polyurethane or a polyisocyanurate polymer, the coreactant is a polyfunctional isocyanate, and the optional solvent is a non-reactive solvent that does not react with the isocyanate, or is reactive solvent that reacts with the isocyanate and become incorporated into the polyurethane or polyisocyanurate.

51. The method of statement 50, wherein the solvent is an aromatic hydrocarbon, an unsaturated hydrocarbon, an ester, a carbonate ester, an ether, a ketone, an amide, a glycol ether, a glycol ester, a glycol ether ester, a halocarbon, or dimethyl sulfoxide (DMSO); or any mixture thereof.

52. The method of statement 51, wherein the aromatic hydrocarbon is toluene, xylene, or a higher-boiling aromatic hydrocarbon mixture; or a mixture thereof.

53. The method of statement 52, wherein the higher-boiling aromatic hydrocarbon mixture is aromatic 150.

54. The method of statement 51, wherein the unsaturated hydrocarbon is limonene.

55. The method of statement 51, wherein the ester is methyl acetate, ethyl acetate, propyl acetate, butyl acetate, t-butyl acetate, methyl glycolate, ethyl glycolate, propyl glycolate, butyl glycolate methyl lactate, ethyl lactate, propyl lactate, butyl lactate, dimethyl succinate, dimethyl glutarate, dimethyl adipate, diisobutyl succinate, diisobutyl glutarate, diisobutyl adipate, methyl 6-hydroxycaproate, methyl 5-hydroxyvalerate, methyl 4-hydroxybutyrate, methyl levulinate, ethyl levulinate, butyrolactone, valerolactone, 3-ethoxy ethyl propionate (EEP), methyl soyate, an isosorbide ester, or a bio-succinic acid ester; or any mixture thereof.

56. The method of statement 51, wherein the ester is an ester derived from a natural fat or oil, or is an ester derived from a carbohydrate, or is an ester comprising a fermentation-derived material.

57. The method of statement 51, wherein the carbonate is dimethyl carbonate or propylene carbonate; or a mixture thereof.

58. The method of statement 51, wherein the ether is tetrahydrofuran or dimethyl isosorbide; or a mixture thereof.

59. The method of statement 51 wherein the ketone is acetone, 2-butanone, methyl isobutyl ketone, diisobutyl ketone, or isophorone; or a mixture thereof.

60. The method of statement 51, wherein the amide is dimethyl formamide (DMF), dimethyl acetamide (DMAC), or N-methylpyrrolidone (NMP); or a mixture thereof.

61. The method of statement 51, wherein the glycol ether is ethylene glycol butyl ether (EB), diethylene glycol butyl ether, or tripropylene glycol methyl ether; or a mixture thereof.

62. The method of statement 51, wherein the glycol ester is ethylene glycol diacetate or propylene glycol diacetate; or a mixture thereof.

63. The method of statement 51, wherein the glycol ether ester is propylene glycol methyl ether acetate, propylene glycol methyl ether propionate, dipropylene glycol methyl ether acetate, ethylene glycol butyl ether acetate, or diethylene glycol butyl ether acetate; or a mixture thereof.

64. The method of statement 51, wherein the halogenated solvent is methylene chloride or p-chlorobenzotrifluoride.

65. The method of any one of statements 51-64, wherein the catalyst is an amine.

66. The method of statement 65, wherein the amine is triethanolamine or diazobicyclooctane, or a mixture thereof.

67. A pre-polymer composition prepared by the method of any one of statements 49-66.

68. A foam composition comprising the polyurethane polymer of statement 42, or the polyisocyanurate polymer of statement 48, or the pre-polymer composition of statement 67; and a blowing agent, and, optionally, a surfactant.

69. The foam composition of statement 68 wherein the blowing agent comprises a hydrocarbon having 3 to 7 carbon atoms, a hydrofluorocarbon, water, or carbon dioxide; or a mixture thereof.

70 The foam composition of statement 69 wherein the hydrofluorocarbon is 1,1,1,3,3-pentafluoropropane (HFC-245fa), 1,1,1,2-tetrafluoroethane (HCF-134a), 1,1-dichloro-1-fluoroethane (HCFC 141-B), chlorodifluoromethane (HCFC R-22), or 1,1,1,3,3-pentafluorobutane (HFC-365mfc); or a combination thereof.

71. The foam composition of statement 69 wherein the hydrocarbon is butane, n-pentane, i-pentane, cyclopentane, hexane, cyclohexane, or any of their alkene analogues; or a combination thereof.

72. A method of preparing a polymer foam composition, comprising combining the pre-polymer composition of statement 67; a blowing agent comprising a hydrocarbon having 3 to 7 carbon atoms, a hydrofluorocarbon, water, or carbon dioxide, or a mixture thereof; and optionally, a surfactant; under conditions suitable for the blowing agent to produce a foamed state in the pre-polymer composition prior to solidification of the pre-polymer composition into the solid polymer material of statement 42 or statement 48.

73. A sealant comprising the polyurethane polymer of statement 42, the polyisocyanurate polymer of statement 48, or the pre-polymer composition of statement 67.

74. A method of sealing an object or a void therein, comprising applying the pre-polymer composition of statement 67 to the object to be sealed, then maintaining the pre-polymer composition on the object under conditions suitable for the pre-polymer composition to form a solid polymer material of statement 42 or 48.

75. An adhesive or binder comprising the polyurethane polymer of statement 42, the polyisocyanurate polymer of statement 48, or the pre-polymer composition of statement 67.

76. A method of causing adhesion or binding of two or more solid objects, comprising applying the pre-polymer composition of statement 67 to the two or more solid objects, placing the two or more solid objects in proximity to each other, and maintaining the pre-polymer composition on the objects in proximity under conditions suitable for the pre-polymer composition to form the solid polymer material of statement 42 or 48.

77. A coating comprising the polyurethane polymer of statement 42, the polyisocyanurate polymer of statement 48, or the pre-polymer composition of statement 67.

78. A method of applying a coating to one or more solid object, comprising applying the pre-polymer composition of statement 67 to the solid object, then, maintaining the pre-polymer composition on the object under conditions suitable for the pre-polymer composition to form the solid polymer material of statement 42 or 48.

79. A coated particulate fertilizer composition, comprising a fertilizer substance in particulate form, with a coating thereon comprising a polyurethane polymer of statement 42 or a polyisocyanurate polymer of statement 48.

80. The coated particulate fertilizer composition of statement 79, wherein the fertilizer substance is urea.

81. The coated particulate fertilizer composition of statement 79, wherein the fertilizer substance is prilled urea.

82. The coated particulate fertilizer composition of any one of statements 79-81, wherein the coated particulate fertilizer is a controlled-release or prolonged-release fertilizer.

83. The coated particulate fertilizer composition of any one of statements 79-82, wherein the coating is biodegradable.

84. The coated particulate fertilizer composition of any one of statements 79-83, wherein the composition further comprises a herbicide, an insecticide, or a fungicide, or any combination thereof.

85. The coated particulate fertilizer composition of any one of statements 79-84, wherein the third component of the polyol composition comprises a polyfunctional aromatic acid, or an anhydride thereof, or an activated ester thereof, or a polyfunctional ester thereof, or a mixture thereof, added in the preparation of the resin composition comprising the polyol.

86. The coated particulate fertilizer composition of statement 85 wherein the composition exhibits a slower release profile of the fertilizer under field conditions than does a comparable composition having a lesser content of aromatic functionality.

87. A method of preparing a coated particulate fertilizer composition, comprising:
(1) heating a byproduct mixture comprising:
    i) a water extract of a cyclohexane oxidation reaction product, optionally concentrated; or,
    ii) a non-volatile residue of a cyclohexane oxidation reaction product, optionally concentrated; or a mixture thereof,
and, one or more polyhydroxy compound, and optionally, a catalyst; optionally under vacuum, or optionally with an inert gas sparge; to remove monofunctional components and water by distillation; to form a polyol composition; then,
(2) combining the polyol composition and a polyfunctional isocyanate, and, optionally, a catalyst, and, optionally, a solvent, under conditions suitable to provide a pre-polymer composition for a polyurethane polymer; and,
(3) coating a fertilizer substance in particulate form with the pre-polymer composition, then maintaining the pre-polymer composition disposed on the fertilizer substance under conditions suitable for the pre-polymer composition to form a solid polyurethane polymer coating;
to provide the coated particulate fertilizer composition.

88. The statement of statement 87, wherein the polyol composition and the polyfunctional isocyanate are combined to provide the pre-polymer composition prior to the step of coating the fertilizer composition therewith.

89. The statement of statement 87, wherein the polyol composition and the polyfunctional isocyanate are separately applied to the fertilizer substance in particulate form, whereupon the pre-polymer composition is formed.

90. A fiber-reinforced composite material comprising a polyurethane polymer of statement 42 or a polyisocyanurate polymer of statement 48 and a fiber substance.

91. The fiber-reinforced composite material of statement 90 wherein the fiber substance is cellulosic.

92. The fiber-reinforced composite material of statement 91, wherein the cellulosic substance comprises wood fibers.

93. A method of preparing a fiber-reinforced composite material, comprising contacting the fiber substance and the pre-polymer composition of statement 67, then maintaining the pre-polymer composition in contact with the fiber substance under conditions suitable for the pre-polymer composition to form the solid polymer material of statement 42 or 48.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:
1. A method of preparing a polyol composition, the method comprising:
heating a byproduct mixture comprising:
i) a water extract of a cyclohexane oxidation reaction product, optionally concentrated; or, ii) a non-volatile residue of a cyclohexane oxidation reaction product, optionally concentrated; or a mixture thereof, and, one or more polyhydroxy compound, and optionally, a catalyst;

optionally under vacuum, or optionally with an inert gas sparge;

to remove monofunctional components and water by distillation.

2. The method of claim 1, further comprising a step of heating the byproduct mixture, optionally under vacuum, or optionally with an inert gas sparge, to remove monofunctional components and water, prior to adding the one or more polyhydroxy compounds, then, after adding the one or more polyhydroxy compounds, continuing to heat the resulting mixture.

3. The method of claim 1 wherein a remaining content of the monofunctional compounds following the step of heating and removal thereof by distillation is about 10% or less, or is about 5% or less, or is about 2% or less, by weight, of the composition.

4. The method of claim 1, wherein the monofunctional components include monocarboxylic acids and monohydric alcohols.

5. The method of claim 1, wherein the polyhydroxy compound comprises a diol, a triol, a tetraol, a saccharide, or a sugar alcohol, or any combination thereof.

6. The method of claim 1, wherein the polyhydroxy compound is ethylene glycol, diethylene glycol, polyethelene glycol, propylene glycol, dipropylene glycol, polypropylene glycol, butanediol, pentanediol, hexanediol, glycerine, trimethylolpropane, pentaerythritol, or sorbitol, or a combination thereof.

7. The method of claim 1, further comprising adding to the byproduct mixture a third component comprising a polyfunctional acid, or an activated ester thereof, or a polyfunctional ester thereof, or an anhydride thereof, or a combination thereof, to the byproduct mixture, then heating and removing monofunctional compounds by distillation.

8. The method of claim 7, wherein the third component comprises terephthalic acid, isophthalic acid, orthophthalic acid, trimellitic acid, pyromellitic acid; the activated ester thereof, the polyfunctional ester thereof, or the anhydride thereof; or any combination thereof.

9. The method of claim 1, further comprising adding to the byproduct mixture a polyfunctional crosslinker or chain extender with two or more reactive hydroxyl or amino functionalities.

10. The method of claim 9, wherein the polyfunctional crosslinker or chain extender is ethylene glycol, diethylene glycol, triethylene glycol, propylene glycol, dipropylene glycol, tripropylene glycol, 1,3-propanediol, 1,3-butanediol, 1,4-butanediol, 1,6-hexanediol, cyclohexane dimethanol, hydroquinone bis(2-hydroxyethyl)ether, neopentyl glycol, glycerol, ethanolamine, diethanolamine, triethanolamine, methyl diethanolamine, phenyl diethanolamine, trimethylolpropane, 1,2,6-hexanetriol, pentaerythritol, N,N,N',N'-tetrakis-(2-hydroxypropyl)ethylenediamine, diethyltoluenediamine, or dimethylthiotoluenediamine; or any mixture thereof.

11. The method of claim 1, comprising adding the catalyst to the byproduct mixture, wherein the catalyst comprises an organometallic compound or a strong acid.

12. The method of claim 11, wherein the organometallic compound is tetraisopropyl titanate or dibutyl tin dilaurate, or the strong acid is toluenesulfonic acid or xylenesulfonic acid.

13. The method of claim 1, further comprising adding a hydrophobic material to the byproduct mixture, then heating and removing monofunctional components by distillation.

14. The method of claim 13, wherein the hydrophobic material comprises a natural oil, a fatty acid or a fatty acid ester derived therefrom; or a synthetic oil; or a mixture thereof.

15. The method of claim 1 wherein the polyol composition has an OH value of about 100 to 500 mg KOH/gm of sample; or, wherein the composition has an acid number of less than 10 mg KOH/gm of sample, or less than 5 mg KOH/gm of sample, or preferably less than 1 mg KOH/gm of sample; or any combination thereof.

16. The method of claim 1 wherein the byproduct mixture is a byproduct mixture of an adipic acid manufacturing process, or is a byproduct mixture of a caprolactam manufacturing process, or is a mixture thereof.

17. A method of preparing a coated particulate fertilizer composition, comprising:
(1) heating a byproduct mixture comprising:
    i) a water extract of a cyclohexane oxidation reaction product, optionally concentrated; or,
    ii) a non-volatile residue of a cyclohexane oxidation reaction product, optionally concentrated; or a mixture thereof,
    and, one or more polyhydroxy compound, and optionally, a catalyst; optionally under vacuum, or optionally with an inert gas sparge; to remove monofunctional components and water by distillation; to form a polyol composition; then,
(2) combining the polyol composition and a polyfunctional isocyanate, and, optionally, a catalyst, and, optionally, a solvent, under conditions suitable to provide a pre-polymer composition for a polyurethane polymer; and,
(3) coating a fertilizer substance in particulate form with the pre-polymer composition; then maintaining the pre-polymer composition disposed on the fertilizer substance under conditions suitable for the pre-polymer composition to form a solid polyurethane polymer coating;

to provide the coated particulate fertilizer composition.

18. The method of claim 17, wherein the polyol composition and the polyfunctional isocyanate are combined to provide the pre-polymer composition prior to the step of coating the fertilizer composition therewith.

19. The method of claim 17, wherein the polyol composition and the polyfunctional isocyanate are separately applied to the fertilizer substance in particulate form, whereupon the pre-polymer composition is formed.

* * * * *